(12) United States Patent
Eylem et al.

(10) Patent No.: US 11,286,620 B2
(45) Date of Patent: Mar. 29, 2022

(54) QUATERNARY AMMONIUM COMPOUND COMPOSITIONS AND METHODS FOR MAKING AND USING SAME

(71) Applicant: The Procter & Gamble Company, Cincinnati, OH (US)

(72) Inventors: Cahit Eylem, West Chester, OH (US); Kevin Patrick Christmas, Mason, OH (US); Michael Scott Prodoehl, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 21 days.

(21) Appl. No.: 16/739,155

(22) Filed: Jan. 10, 2020

(65) Prior Publication Data

US 2020/0224369 A1 Jul. 16, 2020

Related U.S. Application Data

(60) Provisional application No. 62/791,259, filed on Jan. 11, 2019.

(51) Int. Cl.
| | |
|---|---|
| *D21H 17/07* | (2006.01) |
| *D21H 17/09* | (2006.01) |
| *C07C 209/90* | (2006.01) |
| *D21H 27/00* | (2006.01) |
| *C07C 211/63* | (2006.01) |
| *D21H 19/12* | (2006.01) |

(52) U.S. Cl.
CPC .......... *D21H 17/07* (2013.01); *C07C 209/90* (2013.01); *C07C 211/63* (2013.01); *D21H 17/09* (2013.01); *D21H 19/12* (2013.01); *D21H 27/002* (2013.01)

(58) Field of Classification Search
USPC ......................................................... 162/135
See application file for complete search history.

(56) References Cited

U.S. PATENT DOCUMENTS

| | | |
|---|---|---|
| 4,851,141 A | 7/1989 | Demangeon et al. |
| 5,840,403 A | 11/1998 | Trokhan et al. |
| 6,117,525 A | 9/2000 | Trokhan et al. |
| 6,179,961 B1 | 1/2001 | Ficke et al. |
| 6,261,580 B1 | 7/2001 | Lehrter et al. |
| 6,420,013 B1 | 7/2002 | Vinson et al. |
| 6,579,416 B1 | 6/2003 | Vjnson et al. |
| 6,607,637 B1 | 9/2003 | Vinson et al. |
| 6,755,939 B2 | 6/2004 | Vinson et al. |
| 6,797,117 B1 | 9/2004 | McKay et al. |
| 7,282,116 B2 | 10/2007 | Vinson et al. |
| 7,311,853 B2 | 12/2007 | Vinson et al. |
| 2017/0121911 A1 | 5/2017 | Anand et al. |

FOREIGN PATENT DOCUMENTS

| | | |
|---|---|---|
| CA | 2346658 A1 | 4/2000 |
| EP | 0295739 A2 | 12/1988 |
| WO | WO 94/29520 | 12/1994 |
| WO | WO 94/29521 | 12/1994 |
| WO | 0022233 A1 | 4/2000 |

*Primary Examiner* — Mark Halpern
(74) *Attorney, Agent, or Firm* — C. Brant Cook

(57) ABSTRACT

Quaternary ammonium compound compositions and more particularly quaternary ammonium compound compositions including greater than 25% by weight of a quaternary ammonium compound, methods for making same, fibrous structures employing same, and methods for treating fibrous structures with same are provided.

17 Claims, 3 Drawing Sheets

QUATERNARY AMMONIUM COMPOUND COMPOSITIONS AND METHODS FOR MAKING AND USING SAME

FIELD OF THE INVENTION

The present invention relates to quaternary ammonium compound compositions and more particularly to quaternary ammonium compound compositions comprising greater than 25% by weight of a quaternary ammonium compound, methods for making same, fibrous structures comprising same, and methods for treating fibrous structures with same.

BACKGROUND OF THE INVENTION

Quaternary ammonium compound compositions comprising a solid quaternary ammonium compound, for example a quaternary ammonium compound that exhibits a melting point of greater than 30° C. and/or greater than 35° C. and/or at least 38° C., are known in the art. For example, quaternary ammonium compound compositions comprising 20% by weight or less of a quaternary ammonium compound is known. However, there is a need for quaternary ammonium compound compositions comprising greater than 20% by weight, for example greater than 25% by weight of a quaternary ammonium compound, because higher levels of quaternary ammonium compounds in such compositions is advantageous for various reasons; including but not limited to being more efficient than the 20% by weight compositions, delivering equal or better performance, for example in consumer products, such as being used as a softening agent on a surface of a fibrous structure, such as toilet tissue, than the 20% by weight compositions and/or less shipping costs due to shipping less water compared to the 20% by weight compositions.

Previous attempts at formulating quaternary ammonium compound compositions comprising greater than 20% by weight, for example greater than 25% by weight, such as about 44% by weight of a quaternary ammonium compound have been less than successful due to such quaternary ammonium compound compositions exhibiting increases in viscosity resulting in the quaternary ammonium compound compositions exhibiting viscosities of much greater than 250 cP after 14 days as measured according to the Viscosity Test Method described herein. One reason for the increase in viscosity is that such quaternary ammonium compound compositions contain vesicles, for example vesicles such that the quaternary ammonium compound composition exhibits an average particle size distribution larger than is acceptable due to that fact that larger vesicles grow larger and larger during mixing and storage aiding and/or causing the significant increase in viscosity over time. Another possible related reasons are having less than desired number of lamellar quaternary ammonium layers and more than desired trapped water inside vesicles resulting in vesicles with larger average particle size and less continuous phase that are acceptable to support low viscosity high concentration formulations greater than 20% by weight.

As a result of the viscosity negatives associated with such quaternary ammonium compound compositions such compositions were unacceptable for surface application to fibrous structures, such as sanitary tissue products, for example toilet tissue, via non-spray applications, such as via extrusion dies, for example slot extrusion dies, contact or non-contact, in a converting application of a papermaking operation. In addition to the application problems associated with such quaternary ammonium compound compositions, the compositions also exhibited process hygiene issues.

To address the problems, formulators diluted the quaternary ammonium compound compositions by adding additional amounts of water resulting in quaternary ammonium compound compositions comprising 20% by weight of the quaternary ammonium compound instead of 44% by weight of the quaternary ammonium compound. However, the additional water present within the diluted quaternary ammonium compound compositions created different issues relating to fibrous structure properties, for example loss in tensile strength, and/or stretch, such as MD stretch, and/or structure, such as embossments, and/or micro-susceptibility, of the fibrous structures, for example sanitary tissue products, such as toilet tissue.

One problem faced by formulators is how to produce a quaternary ammonium compound composition comprising greater than 25% and/or greater than 30% and/or greater than 35% and/or at least 40% and/or at least 45% and/or at least 50% by weight of a quaternary ammonium compound, and optionally less than 75% and/or less than 70% and/or less than 65% and/or less than 60% and/or less than 55% and/or less than 50% and/or less than 45% and/or less than 40% by weight of water, such that the quaternary ammonium compound composition avoids the negatives, for example viscosity issues, such that the quaternary ammonium compound compositions exhibit viscosities of less than 250 cP after 14 days and/or after 21 days and/or after 28 days and/or after 35 days and/or after 42 days and/or after 49 days and/or after 100 days and/or after 120 days as measured according to the Viscosity Test Method described herein.

Accordingly, there is a need for a quaternary ammonium compound composition comprising greater than 25% by weight of a quaternary ammonium compound such that the quaternary ammonium compound composition avoids the negatives, for example viscosity increases described above that plague known quaternary ammonium compound compositions, methods for making such quaternary ammonium compound compositions, fibrous structures containing such quaternary ammonium compound compositions, and methods for making such fibrous structures.

SUMMARY OF THE INVENTION

The present invention fulfills the need described above by providing a quaternary ammonium compound composition comprising greater than 25% by weight of a quaternary ammonium compound such that the quaternary ammonium compound composition avoids the negatives, for example viscosity increases described above that plague known quaternary ammonium compound compositions, methods for making such quaternary ammonium compound compositions, fibrous structures containing such quaternary ammonium compound compositions, and methods for making such fibrous structures.

One solution to the problem described above is a quaternary ammonium compound composition comprising greater than 25% and/or greater than 30% and/or greater than 35% and/or at least 40% and/or at least 45% and/or at least 50% by weight of a quaternary ammonium compound, and optionally less than 75% and/or less than 70% and/or less than 65% and/or less than 60% and/or less than 55% and/or less than 50% and/or less than 45% and/or less than 40% by weight of water, such that the quaternary ammonium compound composition avoids the negatives, for example viscosity issues, such that the quaternary ammonium compound compositions exhibit viscosities of less than 250 cP after 14 days and/or after 21 days and/or after 28 days and/or after 35 days and/or after 42 days and/or after 49 days and/or after 100 days and/or after 120 days as measured according to the Viscosity Test Method described herein.

It has unexpectedly been found that a quaternary ammonium compound composition comprising greater than 25% and/or greater than 30% and/or greater than 35% and/or at least 40% and/or at least 45% and/or at least 50% by weight of a quaternary ammonium compound, and optionally less than 75% and/or less than 70% and/or less than 65% and/or less than 60% and/or less than 55% and/or less than 50% and/or less than 45% and/or less than 40% by weight of water, can be made by increasing the initial quaternary ammonium compound to water ratio at the time of initial mixing of the quaternary ammonium compound with the water to greater than 2.25:1 and/or greater than 2.3:1 and/or greater than 2.35:1 and/or at least 2.4:1 and/or at least 2.5:1 and/or at least 2.75:1 and/or at least 3:1 and/or subjecting the mixture of the quaternary ammonium compound and water to a temperature of less than 50° C. and/or less than 45° C. and/or less than 40° C. and/or less than 35° C. and/or less than 30° C. and/or greater than 0° C. and/or greater than 10° C. and/or greater than 15° C. and/or greater than 20° C. during the method of making the quaternary ammonium compound composition of the present invention such that the quaternary ammonium compound composition avoids the negatives, for example viscosity issues, such that the quaternary ammonium compound compositions exhibit viscosities of less than 250 cP after 14 days and/or after 21 days and/or after 28 days and/or after 35 days and/or after 42 days and/or after 49 days and/or after 100 days and/or after 120 days as measured according to the Viscosity Test Method described herein.

In one example of the present invention, a quaternary ammonium compound composition comprising:
  a. greater than 25% by weight of a quaternary ammonium compound; and
  b. less than 75% by weight of water;
wherein the quaternary ammonium compound composition exhibits a viscosity of less than 250 cP after 14 days as measured according to the Viscosity Test Method is provided.

In another example of the present invention, a quaternary ammonium compound composition comprising:
  a. greater than 25% but less than 40%, for example from about 31% to about 35%, by weight of a quaternary ammonium compound; and
  b. greater than 60% to less than 75% by weight of water;
wherein the quaternary ammonium compound composition exhibits a particle size distribution viscosity of from about 100 nm to about 50 μm, is provided.

In yet another example of the present invention, a quaternary ammonium compound composition comprising:
  a. greater than 25% but less than 40%, for example from about 31% to about 35%, by weight of a quaternary ammonium compound;
  b. less than 75% by weight of water; and
  c. salt, for example sodium formate;
wherein the quaternary ammonium compound composition exhibits a particle size distribution viscosity of from about 100 nm to about 50 μm, is provided.

In another example of the present invention, a method for making a quaternary ammonium compound composition of the present invention, wherein the method comprises the steps of:
  a. adding a quaternary ammonium compound, for example a quaternary ammonium compound in molten form, such as a quaternary ammonium compound at a temperature above its melting point, to water to form a mixture; and b. cooling the mixture, for example to a temperature of 50° C. or less, such that the quaternary ammonium compound composition is produced is provided.

In another example of the present invention, a method for making a quaternary ammonium compound composition of the present invention, wherein the method comprises the steps of:
  a. adding a quaternary ammonium compound, for example a quaternary ammonium compound in molten form, such as a quaternary ammonium compound at a temperature above its melting point, for example at least 93° C., to water to form a mixture;
  b. cooling the mixture, for example to a temperature of 50° C. or less, such that the quaternary ammonium compound composition is produced; and
  c. adding water, for example water comprising a salt, for example sodium formate to dilute the level of the quaternary ammonium compound in the quaternary ammonium compound composition to less than 40%, for example greater than 25% to less than 40%, such as from about 31% to about 35% is provided.

In another example of the present invention, a fibrous structure comprising a surface comprising a dewatered form of the quaternary ammonium compound composition according to the present invention is provided.

In yet another example of the present invention, a method for treating a fibrous structure, the method comprising the steps of:
  a. providing a fibrous structure; and
  b. applying a quaternary ammonium compound composition according to the present invention to at least one surface of the fibrous structure is provided.

In still another example, a fibrous structure comprising a quaternary ammonium compound, for example greater than 25% and/or greater than 30% and/or greater than 35% and/or at least 40% and/or at least 45% and/or at least 50% by weight of a quaternary ammonium compound, and optionally water, for example less than 75% and/or less than 70% and/or less than 65% and/or less than 60% and/or less than 55% and/or less than 50% and/or less than 45% and/or less than 40% by weight of water, such that the quaternary ammonium compound comprises a plurality of vesicles wherein the quaternary ammonium compound composition exhibits an average particle size distribution of from about 100 nm to about 50 μm.

Accordingly, the present invention provides a novel quaternary ammonium compound composition, a method for making same, a fibrous structure comprising same, and a method for treating a fibrous structure with same.

BRIEF DESCRIPTION OF THE DRAWINGS

Prior Art

Prior Art

DETAILED DESCRIPTION OF THE INVENTION

Definitions

Figure 1:
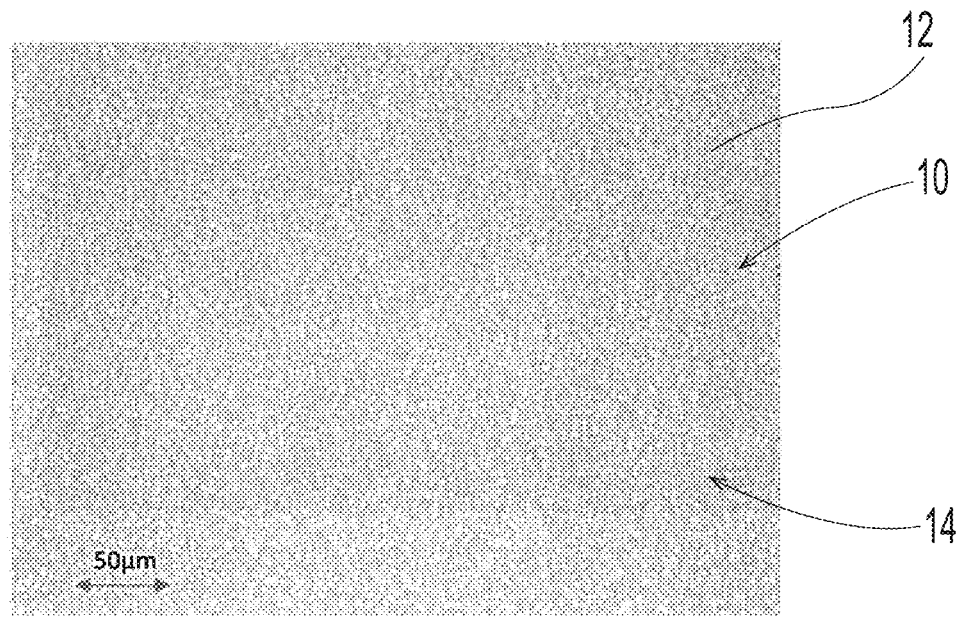
FIG. 1 is an image of an example quaternary ammonium compound composition according to the present invention.

"Sanitary tissue product", which may be referred to herein as a "web", as used herein means a soft, low density (i.e. <about 0.15 g/cm$^3$) article comprising a web comprising one or more fibrous structure plies according to the present invention, wherein the sanitary tissue product is useful as a wiping implement for post-urinary and post-bowel movement cleaning (toilet tissue), for otorhinolaryngological discharges (facial tissue), and multi-functional absorbent and cleaning uses (absorbent towels).

In one example, the sanitary tissue product is a toilet tissue product (toilet tissue), for example a toilet tissue product that is designed to be flushed down toilets, for example residential toilets, such as tank-type toilets, and to disperse within municipal sewer systems and/or septic systems/tanks. Such a toilet tissue product is void of permanent wet strength and/or levels of permanent wet strength agents, for example polyaminoamide-epichlorohydrin (PAE), which would negatively impact the toilet tissue's decay such that the toilet tissue would exhibit a wet strength decay of 25% or less, more typically a wet strength decay of only about 10-15% during a 30 minute soak test. Such a wet strength decay of 25% or less (typically 10-15%) is unacceptable and undesirable for toilet tissue, which is designed to be flushed down toilets and into septic systems/tanks and/or municipal sewer systems. However, the toilet tissue may comprise a temporary wet strength agent such that the toilet tissue exhibits enough wet strength (temporary wet strength) to meet consumer requirements (doesn't fall apart and/or disperse and/or leak through) during use, for example during the brief time the toilet tissue is wet during use and/or exposed to a relatively small amount of water (not saturated) by a consumer (during wiping, for example after urinating), without causing the toilet tissue to exhibit flushability issues compared to the flushability issues a toilet tissue exhibiting permanent wet strength would encounter. In one example, the toilet tissue of the present invention exhibits a wet strength decay of greater than 60% during a 30 minute soak test (and typically even a wet strength decay of at least 40-60% after 2 minutes during the 30 minute soak test), which is considered "temporary wet strength", due to the concerns of flushability issues. Temporary wet strength in paper, for example toilet issue, is achieved by adding temporary wet strength agents, for example glyoxylated polyacrylamide, to the toilet tissue.

In another example, the sanitary tissue product is a paper towel product (paper towel), for example a paper towel product designed to absorb fluids, such as water, while still remaining intact (not dispersing). Paper towel products are designed to not be flushed down toilets and/or to not disperse when wet. Such a paper towel product comprises permanent wet strength and/or levels of permanent wet strength agents, for example polyaminoamide-epichlorohydrin (PAE), which result in the paper towel's exhibiting a wet strength decay of 25% or less, more typically a wet strength decay of only about 10-15% during a 30 minute soak test.

Toilet tissue that exhibits temporary wet strength when disposed in a toilet due to the toilet bowl's water begins decaying, breaking apart into pieces, and dispersing upon saturation of the toilet tissue. Paper towels, which exhibit permanent wet strength, are not suitable to be flushed in toilets because unlike toilet tissue, which exhibits temporary wet strength, paper towels will not decay, break apart into pieces, and disperse upon saturation of the paper towel resulting in the toilet being clogged and/or pipes, septic tank, and municipal sewer systems being "clogged" by the intact paper towel. One reason paper towels require permanent wet strength is that consumers may reuse and rewet a paper towel during use. As result of the issues associated with having permanent wet strength in toilet tissue (bath tissue), one of ordinary skill in the art understands that all bath tissue grades should never include a level of permanent wet strength agent that would result in the toilet tissue (bath tissue) exhibiting permanent wet strength and thus resulting in flushability issues, such as issues with dispersing and/or very low wet strength decay properties.

The sanitary tissue products of the present invention may exhibit a basis weight of greater than 15 g/m$^2$ to about 120 g/m$^2$ and/or from about 15 g/m$^2$ to about 110 g/m$^2$ and/or from about 20 g/m$^2$ to about 100 g/m$^2$ and/or from about 30 to 90 g/m$^2$ as measured according to the respective Basis Weight Test Method described herein. In addition, the sanitary tissue products and/or fibrous structures of the present invention may exhibit a basis weight between about 40 g/m$^2$ to about 120 g/m$^2$ and/or from about 50 g/m$^2$ to about 110 g/m$^2$ and/or from about 55 g/m$^2$ to about 105 g/m$^2$ and/or from about 60 to 100 g/m$^2$ as measured according to the respective Basis Weight Test Method described herein.

The sanitary tissue products, for example toilet tissue products, of the present invention may exhibit a sum of MD and CD dry tensile strength of greater than about 59 g/cm (150 g/in) and/or from about 78 g/cm to about 394 g/cm and/or from about 98 g/cm to about 335 g/cm as measured according to the respective Dry Tensile Strength Test Method described herein. In addition, the sanitary tissue products, for example toilet tissue products, of the present invention may exhibit a sum of MD and CD dry tensile strength of greater than about 196 g/cm and/or from about 196 g/cm to about 394 g/cm and/or from about 216 g/cm to about 335 g/cm and/or from about 236 g/cm to about 315 g/cm as measured according to the respective Dry Tensile Strength Test Method described herein. In one example, the sanitary tissue products, for example toilet tissue products, of the present invention exhibit a sum of MD and CD dry tensile strength of less than about 394 g/cm and/or less than about 335 g/cm as measured according to the respective Dry Tensile Strength Test Method described herein.

In another example, the sanitary tissue products, for example paper towel products, of the present invention may exhibit a sum of MD and CD dry tensile strength of greater than about 196 g/cm and/or greater than about 236 g/cm and/or greater than about 276 g/cm and/or greater than about 315 g/cm and/or greater than about 354 g/cm and/or greater than about 394 g/cm and/or from about 315 g/cm to about 1968 g/cm and/or from about 354 g/cm to about 1181 g/cm and/or from about 354 g/cm to about 984 g/cm and/or from about 394 g/cm to about 787 g/cm as measured according to the respective Dry Tensile Strength Test Method described herein.

The sanitary tissue products, for example toilet tissue products, of the present invention may exhibit an initial sum of MD and CD wet tensile strength of less than about 78 g/cm and/or less than about 59 g/cm and/or less than about 39 g/cm and/or less than about 29 g/cm as measured according to the Wet Tensile Test Method described herein.

The sanitary tissue products, for example paper towel products, of the present invention may exhibit an initial sum of MD and CD wet tensile strength of greater than about 118 g/cm and/or greater than about 157 g/cm and/or greater than about 196 g/cm and/or greater than about 236 g/cm and/or greater than about 276 g/cm and/or greater than about 315 g/cm and/or greater than about 354 g/cm and/or greater than about 394 g/cm and/or from about 118 g/cm to about 1968 g/cm and/or from about 157 g/cm to about 1181 g/cm and/or from about 196 g/cm to about 984 g/cm and/or from about 196 g/cm to about 787 g/cm and/or from about 196 g/cm to about 591 g/cm as measured according to the Wet Tensile Test Method described herein.

The sanitary tissue products of the present invention may exhibit a density (based on measuring caliper at 95 g/in$^2$), which may be referred to as a sheet density or web density to distinguish it from the sanitary tissue product roll's Roll Density, of less than about 0.60 g/cm$^3$ and/or less than about 0.30 g/cm$^3$ and/or less than about 0.20 g/cm$^3$ and/or less than about 0.10 g/cm$^3$ and/or less than about 0.07 g/cm$^3$ and/or less than about 0.05 g/cm$^3$ and/or from about 0.01 g/cm$^3$ to about 0.20 g/cm$^3$ and/or from about 0.02 g/cm$^3$ to about 0.10 g/cm$^3$.

The sanitary tissue products of the present invention may comprise additives such as surface softening agents, for example silicones, quaternary ammonium compounds, aminosilicones, lotions, and mixtures thereof, temporary wet strength agents, permanent wet strength agents, bulk softening agents, wetting agents, latexes, especially surface-pattern-applied latexes, dry strength agents such as carboxymethylcellulose and starch, and other types of additives suitable for inclusion in and/or on sanitary tissue products.

In one example, the sanitary tissue products, for example paper towel products, of the present invention exhibits permanent wet strength, for example the sanitary tissue products comprise a permanent wet strength agent, such as a level of permanent wet strength agent such that the sanitary tissue products exhibit a wet strength decay of less than 25% and/or less than 20% and/or less than 15% and/or from about 5% to about 25% and/or from about 5% to about 20% and/or from about 10% to about 15% during a 30 minute soak test.

In one example, the sanitary tissue products, for example toilet tissue products, of the present invention are void of permanent wet strength, for example the sanitary tissue products exhibit a wet strength decay of greater than 60% and/or greater than 65% and/or greater than 70% and/or greater than 75% and/or greater than 80% during a 30 minute soak test and/or greater than 40% and/or greater than 45% and/or greater than 50% and/or greater than 55% and/or greater than 60% after 2 minutes during the 30 minute soak test. In one example, the sanitary tissue products, for example toilet tissue products, comprise a temporary wet strength agent, for example a level of temporary wet strength agent, such that the sanitary tissue products exhibit the wet strength decay described immediately above.

"Web" and/or "fibrous structure" and/or "fibrous structure ply" as used herein means a structure that comprises a plurality of pulp fibers. In one example, the fibrous structure may comprise a plurality of wood pulp fibers. In another example, the fibrous structure may comprise a plurality of non-wood pulp fibers, for example plant fibers, synthetic staple fibers, and mixtures thereof. In still another example, in addition to pulp fibers, the fibrous structure may comprise a plurality of filaments, such as polymeric filaments, for example thermoplastic filaments such as polyolefin filaments (i.e., polypropylene filaments) and/or hydroxyl polymer filaments, for example polyvinyl alcohol filaments and/or polysaccharide filaments such as starch filaments. In one example, a fibrous structure according to the present invention means an orderly arrangement of fibers alone and with filaments within a structure in order to perform a function. Non-limiting examples of fibrous structures of the present invention include paper.

Non-limiting examples of processes for making fibrous structures include known wet-laid papermaking processes, for example conventional wet-pressed papermaking processes and through-air-dried papermaking processes, and air-laid papermaking processes. Such processes typically include steps of preparing a fiber composition in the form of a suspension in a medium, either wet, more specifically aqueous medium, or dry, more specifically gaseous, i.e. with air as medium. The aqueous medium used for wet-laid processes is oftentimes referred to as a fiber slurry. The fibrous slurry is then used to deposit a plurality of fibers onto a forming wire, fabric, or belt such that an embryonic fibrous structure is formed, after which drying and/or bonding the fibers together results in a fibrous structure. Further processing the fibrous structure may be carried out such that a finished fibrous structure is formed. For example, in typical papermaking processes, the finished fibrous structure is the fibrous structure that is wound on the reel at the end of papermaking, often referred to as a parent roll, and may subsequently be converted into a finished product, e.g. a single- or multi-ply sanitary tissue product.

The fibrous structures of the present invention may be homogeneous or may be layered. If layered, the fibrous structures may comprise at least two and/or at least three and/or at least four and/or at least five layers of fiber and/or filament compositions. In one example, the fibrous structure of the present invention consists essentially of fibers, for example pulp fibers, such as cellulosic pulp fibers and more particularly wood pulp fibers, such as 100% of the fibers present in the fibrous structure are pulp fibers, such as cellulosic pulp fibers and more particularly wood pulp fibers. In another example, the fibrous structure of the present invention comprises fibers and is void of filaments. In still another example, the fibrous structures of the present invention comprise filaments and fibers, such as a co-formed fibrous structure. "Co-formed fibrous structure" as used herein means that the fibrous structure comprises a mixture of at least two different materials wherein at least one of the materials comprises a filament, such as a polypropylene filament, and at least one other material, different from the first material, comprises a solid additive, such as a fiber and/or a particulate. In one example, a co-formed fibrous structure comprises solid additives, such as fibers, such as wood pulp fibers, and filaments, such as polypropylene filaments. "Fiber" and/or "Filament" as used herein means an elongate particulate having an apparent length greatly exceeding its apparent width, i.e. a length to diameter ratio of at least about 10. In one example, a "fiber" is an elongate particulate as described above that exhibits a length of less than 5.08 cm (2 in.) and a "filament" is an elongate particulate as described above that exhibits a length of greater than or equal to 5.08 cm (2 in.).

Fibers are typically considered discontinuous in nature. Non-limiting examples of fibers include pulp fibers, such as wood pulp fibers, and synthetic staple fibers such as polyester fibers.

Filaments are typically considered continuous or substantially continuous in nature. Filaments are relatively longer than fibers. Non-limiting examples of filaments include meltblown and/or spunbond filaments. Non-limiting examples of materials that can be spun into filaments include natural polymers, such as starch, starch derivatives, cellulose and cellulose derivatives, hemicellulose, hemicellulose derivatives, and synthetic polymers including, but not limited to polyvinyl alcohol filaments and/or polyvinyl alcohol derivative filaments, and thermoplastic polymer filaments, such as polyesters, nylons, polyolefins such as polypropylene filaments, polyethylene filaments, and biodegradable or compostable thermoplastic fibers such as polylactic acid filaments, polyhydroxyalkanoate filaments and polycaprolactone filaments. The filaments may be monocomponent or multicomponent, such as bicomponent filaments.

In one example of the present invention, "fiber" refers to papermaking fibers. Papermaking fibers useful in the present invention include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred since they impart a superior tactile sense of softness to tissue sheets made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified fibrous structure. U.S. Pat. Nos. 4,300,981 and 3,994,771 are incorporated herein by reference for the purpose of disclosing layering of hardwood and softwood fibers. Also applicable to the present invention are fibers derived from recycled paper, which may contain any or all of the above categories as well as other non-fibrous materials such as fillers and adhesives used to facilitate the original papermaking.

In one example, the wood pulp fibers are selected from the group consisting of hardwood pulp fibers, softwood pulp fibers, and mixtures thereof. The hardwood pulp fibers may be selected from the group consisting of: tropical hardwood pulp fibers, northern hardwood pulp fibers, and mixtures thereof. The tropical hardwood pulp fibers may be selected from the group consisting of: eucalyptus fibers, acacia fibers, and mixtures thereof. The northern hardwood pulp fibers may be selected from the group consisting of: cedar fibers, maple fibers, and mixtures thereof.

In addition to the various wood pulp fibers, other cellulosic fibers such as cotton linters, rayon, lyocell, trichomes, seed hairs, and bagasse can be used in this invention. Other sources of cellulose in the form of fibers or capable of being spun into fibers include grasses and grain sources.

"Trichome" or "trichome fiber" as used herein means an epidermal attachment of a varying shape, structure and/or function of a non-seed portion of a plant. In one example, a trichome is an outgrowth of the epidermis of a non-seed portion of a plant. The outgrowth may extend from an epidermal cell. In one embodiment, the outgrowth is a trichome fiber. The outgrowth may be a hairlike or bristlelike outgrowth from the epidermis of a plant.

Trichome fibers are different from seed hair fibers in that they are not attached to seed portions of a plant. For example, trichome fibers, unlike seed hair fibers, are not attached to a seed or a seed pod epidermis. Cotton, kapok, milkweed, and coconut coir are non-limiting examples of seed hair fibers.

Further, trichome fibers are different from nonwood bast and/or core fibers in that they are not attached to the bast, also known as phloem, or the core, also known as xylem portions of a nonwood dicotyledonous plant stem. Non-limiting examples of plants which have been used to yield nonwood bast fibers and/or nonwood core fibers include kenaf, jute, flax, ramie and hemp.

Further trichome fibers are different from monocotyledonous plant derived fibers such as those derived from cereal straws (wheat, rye, barley, oat, etc.), stalks (corn, cotton, sorghum, *Hesperaloe funifera*, etc.), canes (bamboo, bagasse, etc.), grasses (esparto, lemon, sabai, switchgrass, etc), since such monocotyledonous plant derived fibers are not attached to an epidermis of a plant.

Further, trichome fibers are different from leaf fibers in that they do not originate from within the leaf structure. Sisal and abaca are sometimes liberated as leaf fibers.

Finally, trichome fibers are different from wood pulp fibers since wood pulp fibers are not outgrowths from the epidermis of a plant; namely, a tree. Wood pulp fibers rather originate from the secondary xylem portion of the tree stem.

"Basis Weight" as used herein is the weight per unit area of a sample reported in $lbs/3000\ ft^2$ or $g/m^2$ (gsm) and is measured according to the respective Basis Weight Test Method described herein.

"Machine Direction" or "MD" as used herein means the direction parallel to the flow of the fibrous structure through the web (fibrous structure) making machine and/or sanitary tissue product manufacturing equipment.

"Cross Machine Direction" or "CD" as used herein means the direction parallel to the width of the web (fibrous structure) making machine and/or sanitary tissue product manufacturing equipment and perpendicular to the machine direction.

"Ply" as used herein means an individual, integral web (fibrous structure).

"Plies" as used herein means two or more individual, integral webs (fibrous structures) disposed in a substantially contiguous, face-to-face relationship with one another, forming a multi-ply fibrous structure and/or multi-ply sanitary tissue product. It is also contemplated that an individual, integral web (fibrous structure) can effectively form a multi-ply fibrous structure, for example, by being folded on itself.

"Embossed" as used herein with respect to a web and/or sanitary tissue product means that a web and/or sanitary tissue product of the present invention has been subjected to a process which converts a smooth surfaced web and/or sanitary tissue product to a decorative surface by replicating a design on one or more emboss rolls, which form a nip through which the web and/or sanitary tissue product passes. Embossed does not include creping, microcreping, printing or other processes that may also impart a texture and/or decorative pattern to a web and/or sanitary tissue product.

"Differential density", as used herein, means a web and/or sanitary tissue product of the present invention that comprises one or more regions of relatively low fiber density, which are referred to as pillow regions, and one or more regions of relatively high fiber density, which are referred to as knuckle regions.

"Densified", as used herein means a portion of a web and/or sanitary tissue product of the present invention that is characterized by regions of relatively high fiber density (knuckle regions).

"Non-densified", as used herein, means a portion of a web and/or sanitary tissue product of the present invention that exhibits a lesser density (one or more regions of relatively lower fiber density) (pillow regions) than another portion (for example a knuckle region) of the web and/or sanitary tissue product.

"Creped" as used herein means creped off of a Yankee dryer or other similar roll and/or fabric creped and/or belt creped. Rush transfer of a web (fibrous structure) alone does not result in a "creped" fibrous structure or "creped" sanitary tissue product for purposes of the present invention.

Quaternary Ammonium Compound Compositions

In one example, the quaternary ammonium compound composition comprises a quaternary ammonium compound, for example greater than 25% and/or greater than 30% and/or greater than 35% and/or greater than 40% and/or greater than 25% to about 70% and/or greater than 30% to about 70% and/or greater than 35% to about 70% and/or greater than 40% to about 70% and/or greater than 40% to about 65% and/or greater than 40% to about 60% and/or greater than 40% to about 55% by weight of the quaternary ammonium compound and optionally water, for example less than 75% and/or less than 70% and/or less than 65% and/or less than 60% and/or less than 50% and/or less than 45% and/or less than 40% and/or from about 25% to less than 75% and/or from about 30% to less than 70% and/or from about 30% to less than 65% and/or from about 30% to less than 60% and/or from about 30% to less than 50% and/or from about 35% to less than 45% by weight of water, and optionally one or more surfactants, such as a nonionic and/or cationic surfactant, for example a nonionic surfactant, capable of creating forming vesicles comprising the quaternary ammonium compound, for example multi-layered vesicles.

Figure 2:
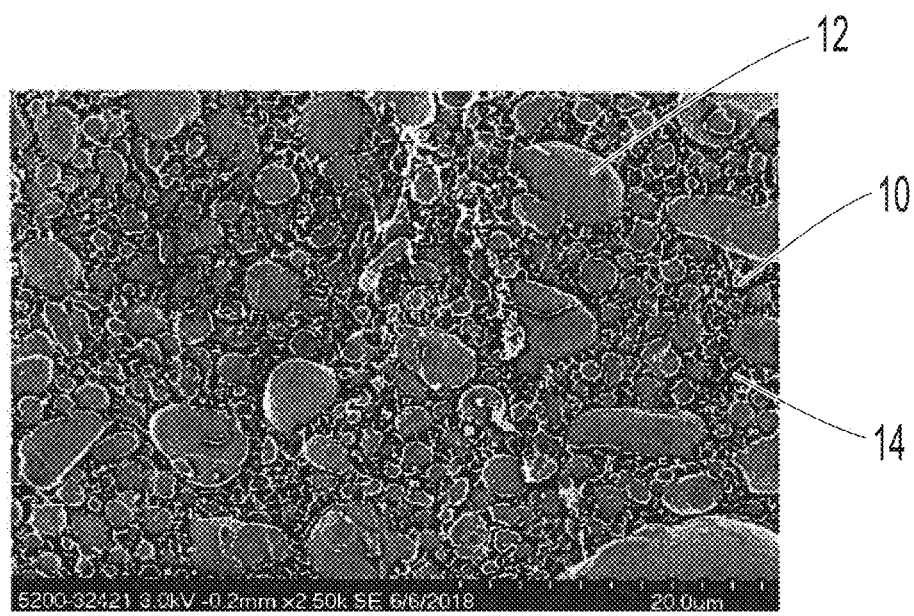
FIG. 2 is an image of an example of a prior art quaternary ammonium compound composition comprising 20% by weight of a quaternary ammonium compound, which is also described in Comparative Example 1 herein.
Figure 3:
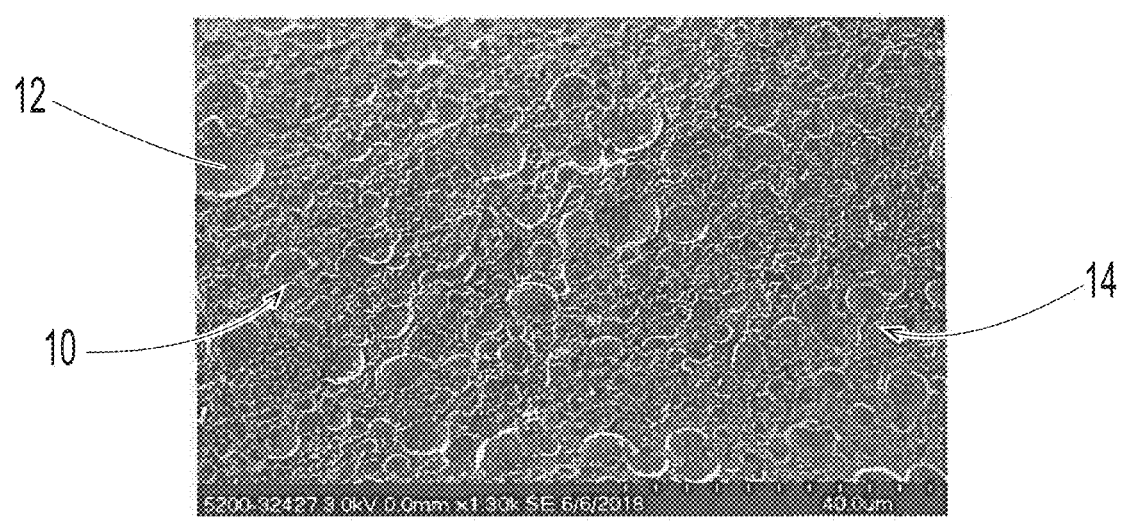
FIG. 3 is an image of an example of a prior art quaternary ammonium compound composition comprising 44% by weight of a quaternary ammonium compound, which is also described in Comparative Example 2 herein.

As shown in FIG. 1, a quaternary ammonium compound composition 10 of the present invention may comprise a plurality of vesicles 12 dispersed throughout a continuous phase 14, for example a continuous phase comprising the water. The vesicles 12 comprise the quaternary ammonium compound and may further comprise water present within the vesicles 12. It has unexpectedly been found that by limiting the initial amount of water in the water and quaternary ammonium compound mixture such that the weight ratio of quaternary ammonium compound to initial water is greater than 2.25:1 and/or greater than 2.3:1 and/or greater than 2.35:1 and/or at least 2.4:1 and/or at least 2.5:1 and/or at least 2.75:1 and/or at least 3:1 and/or subjecting the mixture of the quaternary ammonium compound and water to cooling, for example subjecting the mixture to a temperature of less than 50° C. and/or less than 45° C. and/or less than 40° C. and/or less than 35° C. and/or less than 30° C. and/or greater than 0° C. and/or greater than 10° C. and/or greater than 15° C. and/or greater than 20° C., during the method of making the quaternary ammonium compound composition of the present invention, the vesicles 12 formed in the mixture exhibit a narrower average particle size distribution as measured according to the Average Particle Size Distribution Test Method described herein compared to known quaternary ammonium compound compositions that were made with a quaternary ammonium compound to water weight ratio of 0.8:1 as shown in Prior Art FIGS. 2 and/or 2:1 as shown in Prior Art FIG. 3.

In one example, the quaternary ammonium compound composition exhibits an average particle size distribution of from about 100 nm to about 50 μm and/or from about 1 to about 50 μm and/or from about 1 to about 20 μm and/or from about 1 to about 15 μm and/or from about 1 to about 6 μm as measured according to the Average Particle Size Distribution Test Method.

The pH of such quaternary ammonium compositions may be less than 6 and/or less than 5.5 and/or less than 5 and/or less than 4.5 and/or greater than 2 and/or greater than 2.5 and/or greater than 3 and/or about 3.5 to about 4.5.

In one example, the quaternary ammonium compound compositions of the present invention exhibit a viscosity of less than 250 cP after 14 days and/or after 21 days and/or after 28 days and/or after 35 days and/or after 42 days and/or after 49 days and/or after 100 days and/or after 120 days as measured according to the Viscosity Test Method.

In one example, the quaternary ammonium compound compositions of the present invention provide consumer products, such as fibrous structures, for example sanitary tissue products, such as toilet tissue, and/or textiles, such as fabrics, and/or nonwovens, improved tactile sensation perceived by the user or wearer. Such tactile perceivable softness can be characterized by, but is not limited to, friction, flexibility, and smoothness, as well as subjective descriptors, such as a feeling like lubricious, velvet, silk or flannel.

Quaternary Ammonium Compounds

Non-limiting examples of suitable quaternary ammonium compounds for use in the quaternary ammonium compound compositions of the present invention include quaternary ammonium compounds that exhibit a melting point of greater than 30° C. and/or greater than 35° C. and/or at least 38° C.

Non-limiting examples of suitable quaternary ammonium compounds for use in the quaternary ammonium compound compositions of the present invention include, but are not limited to, quaternary ammonium compounds having the formula:

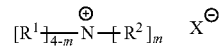

Formula I wherein:

m is 1 to 3; each $R^1$ is independently a $C_1$-$C_6$ alkyl group, hydroxyalkyl group, hydrocarbyl or substituted hydrocarbyl group, alkoxylated group, benzyl group, alkenyl group, or mixtures thereof; each $R^2$ is independently a $C_{14}$-$C_{22}$ alkyl group, hydroxyalkyl group, hydrocarbyl or substituted hydrocarbyl group, alkoxylated group, benzyl group, alkenyl group, or mixtures thereof; and $X^-$ is any compatible anion.

In one example, $X^-$ may be selected from the group consisting of: acetate, chloride, bromide, methyl sulfate, formate, sulfate, nitrate, and mixtures thereof. In another example, $X^-$ is chloride or methyl sulfate. In yet another example, $X^-$ is chloride. In still another example, $X^-$ is methyl sulfate.

In one example, each $R^1$ is independently a $C_1$-$C_6$ alkyl or alkenyl group or mixtures thereof, for example each $R^1$ is independently a $C_1$-$C_6$ alkyl group or mixtures thereof, such as a methyl group.

In one example, each $R^2$ is independently a $C_{16}$-$C_{18}$ alkyl or alkenyl group or mixtures thereof, for example each $R^2$ is independently a straight-chain $C_{16}$-$C_{18}$ alkyl or alkenyl group or mixtures thereof, such as a straight-chain Cis alkyl or alkenyl group or mixtures thereof.

In another example, each $R^2$ is independently a $C_{16}$-$C_{18}$ alkyl group or mixtures thereof, for example each $R^2$ is independently a straight-chain $C_{16}$-$C_{18}$ alkyl group or mixtures thereof, such as a straight-chain Cis alkyl group.

Optionally, the each $R^2$ may be derived from vegetable oil sources. Several types of the vegetable oils (e.g., olive, canola, safflower, sunflower, etc.) can used as sources of fatty acids to synthesize the quaternary ammonium compounds of the present invention. Branched chain actives (e.g., made from isostearic acid) are also effective.

In yet another example, the quaternary ammonium compound of the present invention may be an ester variant, such as a mono-, di-, or trimester variant. Examples of such quaternary ammonium compounds have the following formula:

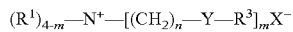

Formula II wherein:
Y is independently —O—(O)C—, —C(O)—O—, —NH—C(O)—, or —C(O)—NH—, or mixtures thereof; m is 1 to 3; n is 0 to 4; each $R^1$ is independently a $C_1$-$C_6$ alkyl group, hydroxyalkyl group, hydrocarbyl or substituted hydrocarbyl group, alkoxylated group, benzyl group, alkenyl group, or mixtures thereof; each $R^3$ is independently a $C_{13}$-$C_{21}$ alkyl group, hydroxyalkyl group, hydrocarbyl or substituted hydrocarbyl group, alkoxylated group, benzyl group, alkenyl group, or mixtures thereof, and $X^-$ is a compatible anion.

In one example, $X^-$ may be selected from the group consisting of: acetate, chloride, bromide, methyl sulfate, formate, sulfate, nitrate, and mixtures thereof. In another example, $X^-$ is chloride or methyl sulfate. In yet another example, $X^-$ is chloride. In still another example, $X^-$ is methyl sulfate.

In one example, Y is independently —O—(O)C— or —C(O)—O—, or mixtures thereof;
m is 2; and n is 2.

In one example, each $R^1$ is independently a $C_1$-$C_3$ alkyl or alkenyl group or mixtures thereof, for example each $R^1$ is independently a $C_1$-$C_3$ alkyl group or mixtures thereof, such as a methyl group.

In another example, each $R^3$ is independently a $C_{13}$-$C_{17}$ alkyl or alkenyl group or mixtures thereof, for example each $R^3$ is independently a $C_{15}$-$C_{17}$ alkyl or alkenyl group or mixtures thereof, such as a straight-chain $C_{15}$-$C_{17}$ alkyl or alkenyl group or mixtures thereof, for example a straight-chain $C_{17}$ alkyl or alkenyl group or mixtures thereof.

In yet another example, each $R^3$ is independently a $C_{13}$-$C_{17}$ alkyl group or mixtures thereof, for example each $R^3$ is a $C_{15}$-$C_{17}$ alkyl group or mixtures thereof, such as a straight-chain $C_{15}$-$C_{17}$ alkyl group or mixtures thereof, for example a straight-chain $C_{17}$ alkyl group.

Optionally, $R^3$ may be derived from vegetable oil sources. Several types of the vegetable oils (e.g., olive, canola, safflower, sunflower, etc.) can be used as sources of fatty acids to synthesize the quaternary ammonium compound. Non-limiting examples include olive oils, canola oils, high oleic safflower, and/or high erucic rapeseed oils can be used to synthesize the quaternary ammonium compounds of the present invention.

Non-limiting examples of ester-functional quaternary ammonium compounds of the present invention include dimethyl sulfate quaternized ester-alkyl ammonium salts having either methyl or ethylhydroxy groups occupying the remainder of the positions on the ammonical nitrogen not substituted with the ester-alkyl functionality. In one example, the quaternary ammonium compound is diester ditallow methyl ethylhydroxy ammonium methyl sulfate. Practical production of this molecule will invariably yield a certain fraction of a monoester-monotallow methyl di(ethylhydroxy) ammonium methyl sulfate and a certain fraction of triester tritallow methyl ammonium methyl sulfate, as well as a certain fraction of monoester, diester, and triester tertiary amines not methylated by the dimethyl sulfate during quaternization. A suitable product of this type has been obtained from Stepan Company as "Agent 2450-15". Another example of a suitable quaternary ammonium compound is diester ditallow dimethyl ammonium methyl sulfate, which analogously will be accompanied by a certain monoester-monotallow dimethyl ethylhydroxy ammonium methyl sulfate and the tertiary amine analogs of these two molecules not being methylated by the dimethyl sulfate.

In another example, the quaternary ammonium compounds of the present invention may be methylated by means of methyl chloride.

As mentioned above, typically, half of the fatty acids present in tallow are unsaturated, primarily in the form of oleic acid. Synthetic as well as natural "tallows" fall within the scope of the present invention. It is also known that depending upon the product characteristic requirements, the degree of saturation for such tallows can be tailored from non hydrogenated to partially hydrogenated or completely hydrogenated. All of above-described saturation levels are expressly meant to be included within the scope of the present invention.

It will be understood that substituents IV, $R^2$ and $R^3$ may optionally be substituted with various groups such as alkoxyl, hydroxyl, or can be branched. In one example each R' independently methyl or hydroxyethyl. In one example, each $R^2$ is independently a $C_{12}$-$C_{18}$ alkyl and/or alkenyl, for example each $R^2$ is a straight-chain $C_{16}$-$C_{15}$ alkyl and/or alkenyl, such as each $R^2$ is independently a straight-chain Cis alkyl or alkenyl. In one example, $R^3$ is a $C_{13}$-$C_{17}$ alkyl and/or alkenyl, such as a straight chain Cis-$C_{17}$ alkyl and/or alkenyl.

In one example, the quaternary ammonium compound is diethyl ester dimethyl ammonium methyl sulfate.

In another example, the quaternary ammonium compound is selected from the group consisting of: dialkyldialkylammonium salts and mixtures thereof.

In another example, the quaternary ammonium compound is selected from the group consisting of: dialkyldimethylammonium salts and mixtures thereof.

In one example, the quaternary ammonium compound comprises a dialkyldimethylammonium salt selected from the group consisting of: mono-ester variants of the dialkyldimethylammonium salt, diester variants of the dialkyldimethylammonium salt, and mixtures thereof.

In one example, the quaternary ammonium compound is selected from the group consisting of: diester ditallow dimethyl ammonium chloride, diester distearyl dimethyl ammonium chloride, monoester ditallow dimethyl ammonium chloride, diester di(hydrogenated)tallow dimethyl ammonium methyl sulfate, diester di(hydrogenated)tallow dimethyl ammonium chloride, monoester di(hydrogenated) tallow dimethyl ammonium chloride, diester di(non hydrogenated)tallow dimethyl ammonium chloride, diester di(touch hydrogenated)tallow dimethyl ammonium chloride (DEDTHTDMAC), diester di(hydrogenated)tallow dimethyl ammonium chloride (DEDHIDMAC), and mixtures thereof.

Such quaternary ammonium compounds may comprise dialkyldimethylammonium salts (e.g., ditallowdimethylammonium chloride, ditallowdimethylammonium methyl sulfate, di(hydrogenated tallow)dimethyl ammonium chloride, etc.) and trialkylmethylammonium salts (e.g., tritallowmethylammonium chloride, tritallowmethylammonium methyl sulfate, tri(hydrogenated tallow)methyl ammonium chloride, etc.), in which IV are methyl groups, $R^2$ of Formula I above are tallow groups of varying levels of saturation, and $X^-$ is chloride or methyl sulfate.

As discussed in Swern, Ed. in Bailey's Industrial Oil and Fat Products, Third Edition, John Wiley and Sons (New York 1964), tallow is a naturally occurring material having a variable composition. Table 6.13 in the above-identified reference edited by Swern indicates that typically 78% or more of the fatty acids of tallow contain 16 or 18 carbon atoms. Typically, half of the fatty acids present in tallow are unsaturated, primarily in the form of oleic acid. Synthetic as well as natural "tallows" fall within the scope of the present invention. It is also known that depending upon the product characteristic requirements, the saturation level of the ditallow can be tailored from non-hydrogenated to partially hydrogenated or to completely hydrogenated. All of above-described saturation levels are expressly meant to be included within the scope of the present invention.

In one example, the quaternary ammonium compound is DEEDMAMS (diethyl ester dimethyl ammonium methyl sulfate), further defined herein wherein the hydrocarbyl chains are derived from tallow fatty acids optionally partially hardened to an iodine value from about 10 to about 60.

Furthermore, in one example, the ester-functional quaternary ammonium compounds of the present invention can optionally contain up to about 10% of the mono(long chain alkyl) derivatives, such as shown in the below formula:

$$(R^1)_2\text{—}N^+\text{—}((CH_2)_2OH)((CH_2)_2OC(O)R^3)X^-$$

as minor ingredients. These minor ingredients can act as emulsifiers.

In one example, depending on the quaternary ammonium compound chosen, the desired application level and other factors as may require a particular level of quaternary ammonium compound in the quaternary ammonium compound composition, the level of quaternary ammonium compound may vary between about 10% of the composition and about 60% of the composition. In one example, the quaternary ammonium compound composition comprises between about 25% and about 50% and/or between about 30% and about 45% by weight of the quaternary ammonium compound.

Surfactant

One or more surfactants and/or two or more surfactants, for example at least one surfactant that functions as a bilayer disrupter, may be added to the quaternary ammonium compound composition of the present invention, such as to the water to form a premix prior to the addition of the quaternary ammonium compound, for example a quaternary ammonium compound in molten form.

Surfactants useful in the compositions of the present invention are surface active materials. Such materials comprise both hydrophobic and hydrophilic moieties. In one example, a hydrophilic moiety is a polyalkoxylated group, such as a polyethoxylated group.

The surfactants may be present in the quaternary ammonium compound composition at a level of between about 1% and about 20% and/or between about 2% and about 15% and/or between about 3% and about 10% by weight of the level of the quaternary ammonium compound.

Non-limiting examples of suitable surfactants include nonionic surfactants derived from saturated and/or unsaturated primary and/or secondary, amine, amide, amine-oxide fatty alcohol, fatty acid, alkyl phenol, and/or alkyl aryl carboxylic acid compounds, for example each having from about 6 to about 22 and/or from about 8 to about 18 carbon atoms in a hydrophobic chain, and/or an alkyl or alkylene chain, wherein at least one active hydrogen of said compounds is ethoxylated with ≤50 and/or ≤30 and/or from about 3 to about 15 and/or from about 5 to about 12 ethylene oxide moieties to provide an HLB of from about 6 to about 20 and/or from about 8 to about 18 and/or from about 10 to about 15. A more complete description of suitable surfactants for use in the quaternary ammonium compound compositions of the present invention can be found in WO 00/22231. In one example, at least one of the surfactants comprises HLB value of less than 12 and/or less than 10 and/or less than 8 and/or less than 12 but greater than 1 and/or less than 10 but greater than 3 and/or less than 8 but greater than 4.

In one example, at least one of the surfactants present in the quaternary ammonium compound composition comprises HLB value of at least 14 and/or at least 15 and/or at least 18 and/or at least 20 and/or at least 14 but less than 25 and/or at least 15 but less than 25 and/or at least 15 but less than 20.

In one example, at least one of the surfactants is selected from the group consisting of: nonionic surfactants, cationic surfactants, and mixtures thereof. In one example, at least one of the surfactants comprises a nonionic surfactant, for example an alcohol ethoxylate, such as a $C_9$-$C_{11}$ alcohol ethoxylate.

In one example, the nonionic surfactant comprises a polyhydroxy fatty acid amide surfactant.

In one example, the quaternary ammonium compound composition comprises from about 0.1 to about 5% and/or from about 0.1 to about 3% and/or from about 0.3 to about 2% and/or from about 0.3 to about 1.5% and/or from about 0.3 to about 1% and/or from about 0.5 to about 0.75% by weight of the one or more surfactants.

Optional Components of the Quaternary Ammonium Compound Composition

Salt (Electrolyte)

Any salt (electrolyte) meeting the general criteria described above for materials suitable for use in the vehicle of the present invention and which is effective in reducing the viscosity of a dispersion of a softening active ingredient in water is suitable for use in the vehicle of the present invention. In particular, any of the known water-soluble electrolytes meeting the above criteria may be included in the vehicle of the quaternary ammonium compound composition of the present invention. When present, the electrolyte can be used in amounts up to about 25% by weight of the quaternary ammonium compound composition, but preferably no more than about 15% by weight of the quaternary ammonium compound composition. Preferably, the level of electrolyte is between about 0.1% and about 10% by weight of the quaternary ammonium compound composition based on the anhydrous weight of the electrolyte. Still more preferably, the electrolyte is used at a level of between about 0.3% and about 1.0% by weight of the quaternary ammonium compound composition. The minimum amount of the electrolyte will be that amount sufficient to provide the desired viscosity. Suitable electrolytes include the halide, nitrate, nitrite, and sulfate salts of alkali or alkaline earth metals, as well as the corresponding ammonium salts. Other useful electrolytes include the alkali and alkaline earth salts of simple organic acids such as sodium formate and sodium acetate, as well as the corresponding ammonium salts. Preferred inorganic electrolytes include the chloride salts of sodium, calcium, and magnesium. Calcium chloride is a particularly preferred inorganic electrolyte for the quaternary ammonium compound composition of the present invention. A particularly preferred organic acid salt-based electrolyte is sodium formate.

In addition to salts (electrolytes), the quaternary ammonium compound composition may further comprise one or more optional ingredients selected from the group consisting of: salts, anti-foaming agents, pH adjusting agents, dispersing agents, chelating agents, and mixtures thereof.

Method for Making Quaternary Ammonium Compound Composition

In one example, the quaternary ammonium compound compositions of the present invention may be made as follows:

a. adding a quaternary ammonium compound, for example a quaternary ammonium compound in molten form, such as a quaternary ammonium compound above its melting point, to water, for example cold water, such as water at 23° C. or less but greater than 0° C. and/or greater than 10° C., to form a mixture; and b. cooling the mixture such that the quaternary ammonium compound compositions of the present invention are produced.

In one example, the step of adding the quaternary ammonium compound to the water results in the mixture exhibiting a weight ratio of quaternary ammonium compound to water of greater than 2.25:1.

In one example, greater than 25% by weight of the quaternary ammonium compound composition of the quaternary ammonium compound is added to less than 75% by weight of the quaternary ammonium compound composition of water to form the mixture.

In one example, one or more surfactants of the present invention may be added to the water prior to adding the quaternary ammonium compound to the water. In addition to the one or more surfactants, an anti-foaming agent and/or pH adjusting agent and/or a salt (electrolyte) and/or a dispersing agent and/or a chelating agent may be added to the water and/or mixture.

A plurality of vesicles are formed in the mixture formed by step a. The vesicles are dispersed throughout a continuous phase, for example the water or at least a portion of the water.

The step of cooling may comprise subjecting the mixture to a temperature of about 50° C. or less and/or from about 50° C. to greater than 10° C. and/or from about 45° C. to greater than 15° C. and/or from about 40° C. to greater than 20° C.

NON-LIMITING EXAMPLES OF METHODS FOR MAKING QUATERNARY AMMONIUM COMPOUND COMPOSITIONS—COMPARATIVE EXAMPLES AND INVENTIVE EXAMPLES

The following Comparative Examples are described below as well as in Table 1 below.

Comparative Example 1

Target batch size is 19517 lbs. Processing tank used is a 2300 gal., jacketed, vertical cylindrical, stainless steel tank with mixing achieved via counter rotating style agitation with elephant ear type paddle on center shaft pitched at approximately 45 degrees.

4817 lbs. hot deionized water (at least 90° C.) added to processing tank and mixing started; 20 Hz (QUAT/Starting Water Ratio=0.8:1). While mixing, 2.73 lbs. fluorescent agent, for example Tinopal CBS-X, which is optional, is added to the processing tank. Tinopal is introduced between mixing blades to avoid coating blades. While mixing, 44.4 lbs. of a surfactant, for example Tomadol 91-8, and 35.1 lbs. of an anti-foaming agent, for example Xiameter AFE 2310, are added to the processing tank. Then mixed for 5 minutes then 76.1 lbs. of 35% sulfuric acid solution is added to the processing tank. Next, the temperature is adjusted to 93° C. and the mixing is increased to 40 Hz. Then 5670 lbs. (350-400 lbs/min) of molten quaternary ammonium compound (at least 93° C.), for example DXP 5558-66, is added to the processing tank while mixing. The processing tank is then cooled to 66-77° C. via a cooling jacket. 1312 lbs. (100-125 lbs/min) 3% salt solution, for example sodium formate solution, is added and the mix speed is adjusted to 20 Hz. Followed by adding 125 lbs. of a dispersing agent, for example Texcare 4060, and adjusting the mix speed to 35 Hz, and mixed for 15 minutes. The temperature is then adjusted to a maximum of 71° C. 3615 lbs. (100-125 lbs/min.) 3% salt solution, for example sodium formate solution, is added to the processing tank while mixing. 4.35 lbs. of a surfactant, for example Tomadol 91-8, is added to the processing tank while mixing. Then 4.39 lbs. of a chelating agent, for example DTPA, such as Versenex 80, is added to the processing tank and mixed for 15 minutes. The processing tank is then cooled to 40° C. After which, 3615 lbs. (100-125 lbs/min.) 3% salt solution, for example sodium formate solution, is added to the processing tank and mixed for 15 minutes. An in-process check of viscosity is then performed. The viscosity is then adjusted, if needed, to a target level of less than 25 cps using suitable increments of 97.6 lbs. of 25% salt solution, for example sodium formate solution, based on the actual batch viscosity.

Comparative Example 2

Target batch size is 43.15 lbs. Processing container used is a 5 gallon plastic bucket with mixing achieved via overhead mixer with impeller. Height is adjusted so impeller was near the bottom of the bucket. Mixing speed is adjusted as needed to achieve an active rolling over of the formulation (batch).

A hot aqueous premix is created by combining 9.87 lbs. of deionized water (QUAT/Starting Water Ratio=1.9:1), 5.87 g of an optional fluorescent agent included for detection purposes, for example Tinopal CBS-X, 97.9 g of a surfactant, for example Tomadol 91-8, 48.9 g of an anti-foaming agent, for example Xiameter AFE 2310, and 164 g sulfuric acid solution (35%) in a stainless steel beaker. Premix is heated on a hot plate to about 90° C. and mixed by stir bar until dissolved/dispersed. The hot premix is then added to the processing container. Mixing with the overhead mixer is started. 26.3 lbs. of molten quaternary ammonium compound (at least 93° C.), for example DXP 5558-66, is added to processing container. Mixer speed is adjusted to maintain adequate mixing. Mixing is aided throughout the process by manually stirring with a large spatula. Once well mixed, 1.8 lbs. of 3% salt solution, for example sodium formate solution, is added to the processing containing and mixed well using overhead mixer and manual stirring. Then 270 g of a dispersing agent, for example Texcare 4060, is added to the processing container and mixed well using overhead mixer and manual stirring. Next 274 g of 25% salt solution, for example sodium formate solution, is added to the processing container and mixed well using overhead mixer and manual stirring. Then 411 g deionized water, is added to the processing container and mixed well using overhead mixer and manual stirring. Next 9.79 g of a surfactant, for example Tomadol 91-8, is added to the processing container and mixed well using overhead mixer and manual stirring. 25.4 g of a chelating agent, for example DTPA, such as Versenex 80, is added to the processing container and mixed well using overhead mixer and manual stirring. Then 393 g deionized water is added to the processing container and mixed well using overhead mixer and manual stirring. Then 162 g of 3% salt solution, for example sodium formate solution, is added to the processing container and mixed well using overhead mixer and manual stirring.

Comparative Example 3

Target batch size was 16964 lbs. Processing tank used was a 2300 gal., jacketed, vertical cylindrical, stainless steel tank with mixing achieved via counter rotating style agitation with elephant ear type paddle on center shaft pitched at approximately 45 degrees.

3830 lbs. hot deionized water (minimum 195 F) added to processing tank and mixing started; 20 Hz (QUAT/Starting Water Ratio=1.9:1). While mixing, 5 lbs. Tinopal CBS-X added. Tinopal introduced between mixing blades to avoid coating blades. While mixing, 85 lbs. of a surfactant, for example Tomadol 91-8, and 42 lbs. of an anti-foaming agent, for example Xiameter AFE 2310, are added to the processing tank and mixed. After mixing for 5 minutes 140 lbs. of 35% sulfuric acid solution to is added to the processing tank. The temperature of the processing tank is set to 93° C. and mixing speed is increased to 40 Hz. 10390 lbs. (350-400 lbs/min) molten quaternary ammonium compound (at least 93° C.), for example DXP 5558-66, is added to the processing tank while mixing. The processing tank is cooled 151-171F via cooling jacket after the quaternary ammonium compound is added. 705 lbs. (100-125 lbs/min) of 3% salt solution, for example sodium formate solution, is added to the processing tank and the mixing speed is adjusted to 20 Hz. 235 lbs. of a dispersing agent, for example Texcare 4060, is added to the processing tank and the mixing speed is adjusted to 35 Hz and mixed for 15 minutes. Adjust the temperature to a maximum of 160 F. 240 lbs. (100-125 lbs/min) of 25% salt solution, for example sodium formate solution, is added to the processing tank while mixing. 355 lbs. deionized water is added to the processing tank. 8.5 lbs. of a surfactant, for example Tomadol 91-8, is added to the processing tank while mixing. 5 lbs. of a chelating agent, for example DTPA, such as Versenex 80, is added to the processing tank and mix for 15 minutes. The processing tank is then cooled to 105 F. 340 lbs. of deionized water is then added to the processing tank and mixed for 15 minutes. Performed in-process check of viscosity is conducted. Then 850 lbs. (100-125 lbs/min.) of 25% salt solution, for example sodium formate solution, while mixing. Additional surfactant, for example Tomadol 91-8 (170 lbs.), 35% sulfuric acid solution (680 lbs.), and 25% salt solution, for example sodium formate solution (650 lbs.), is then added to the processing tank to obtain the low quaternary ammonium compound composition viscosity.

TABLE 1

| Ingredients | Comparative Example 1 % wt | Comparative Example 2 % wt | Comparative Example 3 % wt |
|---|---|---|---|
| Quaternary Ammonium Compound | 20.08 | 43.76 | 38.83 |
| PEG400 (comes along with the quaternary ammonium compound) | 8.61 | 18.75 | 16.64 |
| Surfactant (Tomadol 91-8) | 0.25 | 0.56 | 1.41 |
| Salt solution (Sodium Formate) | 1.34 | 1.1 | 2.44 |
| Fluorescent Agent (Tinapol CBS) | 0.01 | 0.03 | 0.03 |
| Anti-Foaming Agent (Xiameter AFE 2410) | 0.025 | 0.03 | 0.02 |

TABLE 1-continued

| Ingredients | Comparative Example 1 % wt | Comparative Example 2 % wt | Comparative Example 3 % wt |
|---|---|---|---|
| Chelating Agent (Versenex 80) | 0.024 | 0.13 | 0.03 |
| Dispersing Agent (Texcare 4060) | 0.256 | 0.57 | 0.50 |
| pH Adjusting Agent (Sulfuric Acid) | 0.1365 | 0.3 | 1.53 |
| DI Water | 69.268 | 35.34 | 38.56 |
| Final pH | 4.2 | 4.3 | 4.3 |
| Cooling | No | No | No |
| QUAT/Initial Water Ratio | 0.8:1 | 1.9:1 | 1.9:1 |

Inventive Examples of the quaternary ammonium compound composition of the present invention are described below. Such inventive quaternary ammonium compound compositions of the present invention are low viscosity, high active fatty quaternary ammonium compound water dispersion, which in one example provide product benefits, when applied to a sanitary tissue product, for example toilet tissue, as a surface softening agent compared to known quaternary ammonium compound compositions such as described in the Comparative Examples. In addition, in one example the inventive quaternary ammonium compound compositions of the present invention provide process hygiene benefits by exhibiting less or no build-up on manufacturing equipment, for example rollers, in a papermaking manufacturing line compared to known quaternary ammonium compound compositions such as described in the Comparative Examples.

Inventive Example 1—Quaternary Ammonium Compound Composition (40% Active)

A 5 gallon batch of a quaternary ammonium compound composition according to the present invention is made in a 5 gallon plastic bucket with mixing achieved via overhead mixer with impeller. Height is adjusted so impeller was near the bottom of the bucket ("process tank") as follows. Add required amount of cold deionized water, for example deionized water at a temperature of 10 to 18° C. (11.74% of batch) to the process tank and begin mixing at 20 Hz. If water is not within the temperature range, then adjust the temperature accordingly. Ensure that the water temperature is 10 to 18° C. before proceeding. Process tank is continued to be chilled, as necessary, throughout process to maintain the temperature of its contents at a temperature of 10 to 18° C. Next, weigh and add required amounts of 100% active Tinopal CBS-X (0.02% of batch), 100% active of a surfactant (for example Tomadol 91-8 (0.51% of batch)), and 10% active of an anti-foaming agent (for example Xiameter AFE (0.26% of batch)) to the process tank, in this order, and mix for 5 minutes. Then, add required 35% sulfuric acid solution (0.86% of batch) to the process tank and mix for 10 minutes. Adjust mixing speed to 40 Hz. Next, add required amount of 70% active of a quaternary ammonium compound ("QUAT") (for example DXP 5558-66, which is DEED-MAMS, (Paperquat) (57.14% of batch)) to the process tank. DXP 5558-66 is added to the process tank at 350-485 lbs./min at 93° C. (90-102° C.) (QUAT/Water Ratio=3.4:1, which in this case means DEEDMAMS/Water Ratio=3.4:1).

Continue mixing and cooling batch until temperature of batch reaches 46° C. or less, for example 32 to 46° C. Next, add required amount of 3% salt solution (for example sodium formate solution (4.19% of batch)) to the process tank at 100-125 lbs./min Adjust mixing speed to 20 Hz. Next, add required amount of 40% active a dispersing agent (for example Texcare 4060 (1.44% of batch)) to the process tank and adjust mixing speed to 35 Hz. Mix for 15 minutes. Then add required amount of 25% salt solution (for example sodium formate solution (1.45% of batch)) to the process tank at 100-125 lbs./min. Next, add required amount of deionized water (2.16% of batch) to the process tank. After that, weigh and add required amount of 100% active of a surfactant (for example Tomadol 91-8 (0.06% of batch)) to the process tank. Next, cool formulation to ensure that the quaternary ammonium compound (DXP 5588-66) is not in a melted state, for example cool to about 40° C. before proceeding.

After cooling, weigh and add required amount of 40% active Versenex 80 (0.03% of batch) to the process tank. Then add required amount of deionized water (3.36% of batch) to the process tank and mix for 15 minutes. Next add required amount of 25% salt solution (for example sodium formate solution (0.58% of batch)) to the process tank. Next weigh and add required amount of 35% sulfuric acid solution (0.09% of batch) to the process tank and mix for 15 minutes. Followed by adding required amount of 25% salt solution (for example sodium formate solution (1.05% of batch)) to the process tank. Next add required amount of deionized water (15.06% of batch) to the process tank and mix for at least 10 minutes. After mixing, test batch for % quaternary ammonium compound activity and adjust with additional deionized water to reach 40% quaternary ammonium compound activity. The resulting quaternary ammonium compound composition is a 40% active quaternary ammonium compound emulsion having a 327 mM salt (for example sodium formate) concentration.

The temperature of the batch during the process should remain below the cloud point of the surfactant added, for example in the case of Tomadol 91-8, the batch temperature should remain below 80° C. (Tomadol 91-8's cloud point).

Table 2 below is a summary of the materials added to make the quaternary ammonium compound composition of this Inventive Example 1 and the order of addition from top to bottom.

TABLE 2

| Material | Target Material % | Target wt. (g) |
|---|---|---|
| Deionized water | 11.74 | 2222.60 |
| Fluorescent agent (Tinopal) | 0.02 | 3.74 |
| Surfactant (Tomadol 91-8) | 0.51 | 96.39 |
| Anti-foaming agent (Xiameter AFE-2410) | 0.26 | 48.76 |
| Sulfuric acid solution | 0.86 | 163.29 |
| Quaternary ammonium compound (DXP 5558-66) | 57.14 | 10818.18 |
| Salt solution (Sodium Formate (3%)) | 4.19 | 793.79 |
| Dispersing agent (Texcare 4060) | 1.44 | 272.16 |
| Salt solution (Sodium Formate (25%)) | 1.45 | 274.42 |
| Deionized water | 2.16 | 408.23 |
| Surfactant (Tomadol 91-8) | 0.06 | 11.34 |
| Chelating agent (VERSENEX 80) | 0.03 | 5.67 |
| Deionized water | 3.36 | 636.16 |
| Salt solution (Sodium Formate (25%)) | 0.58 | 110.00 |
| Sulfuric acid solution | 0.09 | 17.01 |
| Salt solution (Sodium Formate (25%)) | 1.05 | 198.45 |
| Deionized water | 15.06 | 2851.96 |

Inventive Example 2—Quaternary Ammonium Compound Composition

Target batch size was 400 g. Processing container used is a 400 mL tri-pour beaker with mixing achieved via overhead mixer with impeller. Height is adjusted so impeller is near the bottom of the beaker. Mixing speed is adjusted as needed to achieve an active rolling over of the formulation. Batch cooling is achieved via mixing at 23° C.

A room temperature (23° C.) aqueous premix is created by combining 67 g deionized water (QUAT/Starting Water Ratio=2.4:1), 0.125 g fluorescent agent, for example Tinopal CBS-X, 2.05 g surfactant, for example Tomadol 91-8, 1.05 g anti-foaming agent, for example Xiameter AFE 2310, and 3.42 g sulfuric acid solution (35%) in a tri-pour beaker and mixing by overhead mixer until dissolved/dispersed. 228.57 g molten quaternary ammonium compound (at least 82° C.), for example DXP 5558-66, is added to the beaker. Mixer speed is adjusted to maintain adequate mixing. Mixing is aided throughout the process by manually stirring with a spatula. The batch is mixed and then waited for bulk temperature of batch to reach about 43 to 49° C. 16.78 g of 3% salt solution, for example sodium formate solution, is added to the beaker and mixed well using overhead mixer and manual stirring. 5.83 g of dispersing agent, for example Texcare 4060, is added to a beaker and mixed well using overhead mixer and manual stirring. 5.84 g of 25% salt solution, for example sodium formate solution, is added to the beaker and mixed well using overhead mixer and manual stirring. 8.57 g deionized water is added to the beaker and mixed well using overhead mixer and manual stirring. 0.31 g of surfactant, for example Tomadol 91-8, is added to the beaker and mixed well using overhead mixer and manual stirring. 13.47 g deionized water is added to the beaker and mixed well using overhead mixer and manual stirring. 2.29 g of 25% salt solution, for example sodium formate solution, is added to the beaker and mixed well using overhead mixer and manual stirring. 0.40 g of sulfuric acid solution (35%) is added to the beaker and mixed well using overhead mixer and manual stirring. 4.19 g of 25% salt solution, for example sodium formate solution, is added to the beaker and mixed well using overhead mixer and manual stirring. 40.02 g deionized water is added to the beaker and mixed for at least 5 minutes.

Table 3 below is a summary of the materials added to make the quaternary ammonium compound composition of this Inventive Example 2 and the order of addition from top to bottom.

TABLE 3

| Ingredients | Inventive Example 2 % wt |
|---|---|
| Quaternary Ammonium Compound | 40.01 |
| PEG400 (comes along with the quaternary ammonium compound) | 17.15 |
| Surfactant (Tomadol 91-8) | 0.59 |
| Salt solution (Sodium Formate) | 0.91 |
| Fluorescent Agent (Tinopal CBS) | 0.03 |
| Anti-Foaming Agent (Xiameter AFE 2410) | 0.03 |
| Chelating Agent (Versenex 80) | 0.00 |
| Dispersing Agent(Texcare 4060) | 0.58 |
| pH Adjusting Agent (Sulfuric Acid) | 0.33 |
| Deionized Water | 40.37 |
| Final pH | 4.3 |
| Cooling | Yes |
| QUAT/Initial Water Ratio | 2.4:1 |

Inventive Example 3—Quaternary Ammonium Compound Composition 35% Active—Batch

To make this material, a required amount of the quaternary ammonium compound composition made in Inventive Example 1, which contains 327 mM salt, for example sodium formate, (87.50% of batch) is added to a 5 gallon plastic bucket with mixing achieved via overhead mixer with impeller. Height is adjusted so impeller was near the bottom of the bucket. A required amount of deionized water (12.23% of batch) and 100% active salt solution, for example sodium formate solution, (0.27% of batch) are added to the bucket. Ideally, the required amount of salt solution should be dissolved in the required amount of deionized water (2.17% solution) prior to adding to the bucket. Mix the batch to obtain homogeneity. The final "adjusted" (salt solution, for example sodium formate solution is added) salt, for example sodium formate, concentration is 327 mM.

Table 4 below is a summary of the materials added to make the quaternary ammonium compound composition of this Inventive Example 3 and the order of addition from top to bottom.

TABLE 4

| Material | Target Material % | Target wt. (g) |
| --- | --- | --- |
| Quaternary Ammonium Compound Composition - Inventive Example 1 | 87.50 | 16560.24 |
| Salt solution (Sodium Formate) | 0.27 | 51.34 |
| Deionized Water | 12.23 | 2315.48 |

Inventive Example 4—Quaternary Ammonium Compound Composition 35% Active—Batch

To make this material, a required amount of the quaternary ammonium compound composition made in Inventive Example 1, which contains 327 mM salt, for example sodium formate, (87.50% of batch) is added to a 5 gallon plastic bucket with mixing achieved via overhead mixer with impeller. Height is adjusted so impeller was near the bottom of the bucket. A required amount of deionized water (12.50% of batch) is added to the bucket. Mix to obtain homogeneity. Final "not adjusted" (no salt solution, for example sodium formate solution is added) salt, for example sodium formate, concentration is 242 mM.

Table 5 below is a summary of the materials added to make the quaternary ammonium compound composition of this Inventive Example 4 and the order of addition from top to bottom.

TABLE 5

| Material | Target Material % | Target wt. (g) |
| --- | --- | --- |
| Quaternary Ammonium Compound Composition - Inventive Example 1 | 87.50 | 16561.17 |
| Deionized Water | 12.50 | 2365.88 |

Inventive Example 5—Quaternary Ammonium Compound Composition 35% Active—In-Line

To make this material, the quaternary ammonium compound composition made in Inventive Example 1, which contains 327 mM salt, for example sodium formate, (87.50% of batch) is placed into a first tank to be dosed into a supply line using a first pump. A 2.17% salt solution, for example sodium formate solution, is made from 100% active salt solution, for example sodium formate solution, dissolve in deionized water is placed into a second tank to be dosed into the supply line using a second pump. The first pump is set at 87.5% of total target flow and the second pump is set at 12.5% of total target flow. The pump flow rate ratio (First Pump:Second Pump) is 7:1. Final "adjusted" (salt solution, for example sodium formate solution is added) salt, for example sodium formate, concentration is 327 mM.

Inventive Example 6—Quaternary Ammonium Compound Composition 35% Active—In-Line

To make this material, the quaternary ammonium compound composition made in Inventive Example 1, which contains 327 mM salt, for example sodium formate, (87.50% of batch) is placed into a first tank to be dosed into a supply line using a first pump. Deionized water is placed into a second tank to be dosed into the supply line using a second pump. The first pump is set at 87.5% of total target flow and the second pump is set at 12.5% of total target flow. The pump flow rate ratio (First Pump:Second Pump) is 7:1. Final "not adjusted" (no salt solution, for example sodium formate solution is added) salt, for example sodium formate, concentration is 242 mM.

Inventive Example 7—Quaternary Ammonium Compound Composition 31% Active—Batch

To make this material, the quaternary ammonium compound composition made in Inventive Example 1, which contains 327 mM salt, for example sodium formate, (77.50% of batch) is added to a 5 gallon plastic bucket with mixing achieved via overhead mixer with impeller. Height is adjusted so impeller was near the bottom of the bucket. A required amount of deionized water (22.01% of batch) and 100% active salt solution, for example sodium formate solution, (0.49% of batch) is added to the bucket. Ideally, the required amount of salt solution, for example sodium formate solution, should be dissolved in the required amount of deionized water (2.17% solution) prior to adding to the bucket. Mix to obtain homogeneity. Final "adjusted" (salt solution, for example sodium formate solution is added) salt, for example sodium formate, concentration is 327 mM.

Table 6 below is a summary of the materials added to make the quaternary ammonium compound composition of this Inventive Example 7 and the order of addition from top to bottom.

TABLE 6

| Material | Target Material % | Target wt. (g) |
| --- | --- | --- |
| Quaternary Ammonium Compound Composition - Inventive Example 1 | 77.50 | 14669.40 |
| Salt solution (Sodium Formate) | 0.49 | 92.49 |
| Deionized Water | 22.01 | 4165.16 |

Inventive Example 8—Quaternary Ammonium Compound Composition 31% Active—Batch

To make this material, the quaternary ammonium compound composition made in Inventive Example 1, which contains 327 mM salt, for example sodium formate, (77.50% of batch) is added to a 5 gallon plastic bucket with mixing achieved via overhead mixer with impeller. Height is adjusted so impeller was near the bottom of the bucket. A required amount of deionized water (22.50% of batch) is added to the bucket. Mix to obtain homogeneity. Final "not adjusted" (no salt solution, for example sodium formate solution is added) salt, for example sodium formate, concentration is 191 mM.

Table 7 below is a summary of the materials added to make the quaternary ammonium compound composition of this Inventive Example 8 and the order of addition from top to bottom.

TABLE 7

| Material | Target Material % | Target wt. (g) |
|---|---|---|
| Quaternary Ammonium Compound Composition - Inventive Example 1 | 77.50 | 14668.47 |
| Deionized Water | 22.50 | 4258.59 |

Inventive Example 9—Quaternary Ammonium Compound Composition (31% Active—In-Line To make this material, the quaternary ammonium compound composition made in Inventive Example 1, which contains 327 mM salt, for example sodium formate, (87.50% of batch) is placed into a first tank to be dosed into a supply line using a first pump. A 2.17% salt solution, for example sodium formate solution, is made from 100% active salt solution, for example sodium formate solution, dissolve in deionized water is placed into a second tank to be dosed into the supply line using a second pump. The first pump is set at 77.5% of total target flow and the second pump is set at 22.5% of total target flow. The pump flow rate ratio (First Pump:Second Pump) is 3.44:1. Final "adjusted" (salt solution, for example sodium formate solution is added) salt, for example sodium formate, concentration is 327 mM.

Inventive Example 10—Quaternary Ammonium Compound 31% Active—In-Line

To make this material, the quaternary ammonium compound composition made in Inventive Example 1, which contains 327 mM salt, for example sodium formate, (87.50% of batch) is placed into a first tank to be dosed into a supply line using a first pump. Deionized water is placed into a second tank to be dosed into the supply line using a second pump. The first pump is set at 77.5% of total target flow and the second pump is set at 22.5% of total target flow. The pump flow rate ratio (First Pump:Second Pump) is 3.44:1. Final "not adjusted" (no salt solution, for example sodium formate solution is added) salt, for example sodium formate, concentration is 191 mM.

Fibrous Structure Comprising Quaternary Ammonium Compound Composition

In one example, the quaternary ammonium compound composition of the present invention may be applied to one or more surfaces of a fibrous structure, for example a sanitary tissue product, such as toilet tissue to provide tactile benefits, for example surface softening benefits.

In one example, the fibrous structure comprises a surface comprising a dewatered form of the quaternary ammonium compound composition of the present invention.

In one example, the fibrous structure comprises fibers, for example pulp fibers, such as wood pulp fibers. In one example, the fibrous structure comprises a structured fibrous structure ply, for example an ATMOS fibrous structure ply, a NTT fibrous structure ply, and/or a through-air-dried fibrous structure ply.

In one example, the fibrous structure may comprise a through-air-dried fibrous structure ply, such as a creped through-air-dried fibrous structure ply and/or an uncreped through-air-dried fibrous structure ply.

In one example, the fibrous structure may comprise a fabric creped fibrous structure ply and/or a belt creped fibrous structure ply.

In one example, the fibrous structure may comprise a conventionally wet pressed fibrous structure ply.

Method for Treating a Fibrous Structure

A fibrous structure comprising a surface comprising a quaternary ammonium compound composition may be made by the following steps:

a. providing a fibrous structure; and
b. applying a quaternary ammonium compound composition according to the present invention to at least one surface and/or two surfaces of the fibrous structure.

In one example, the step of applying comprises the step of applying the quaternary ammonium compound composition to at least one dry surface of the fibrous structure, such as during converting of the fibrous structure in a papermaking operation.

In one example, the step of applying comprises delivering the quaternary ammonium compound composition to the surface from an extrusion die, for example a slot extrusion die.

In one example, the quaternary ammonium compound composition may exhibit a temperature of greater than 0° C. and/or greater than 10° C. to about 45° C. in the step of applying to the surface.

In another example, the quaternary ammonium compound composition may exhibit a temperature of greater than 50° C. in the step of applying to the surface.

Figure 4:
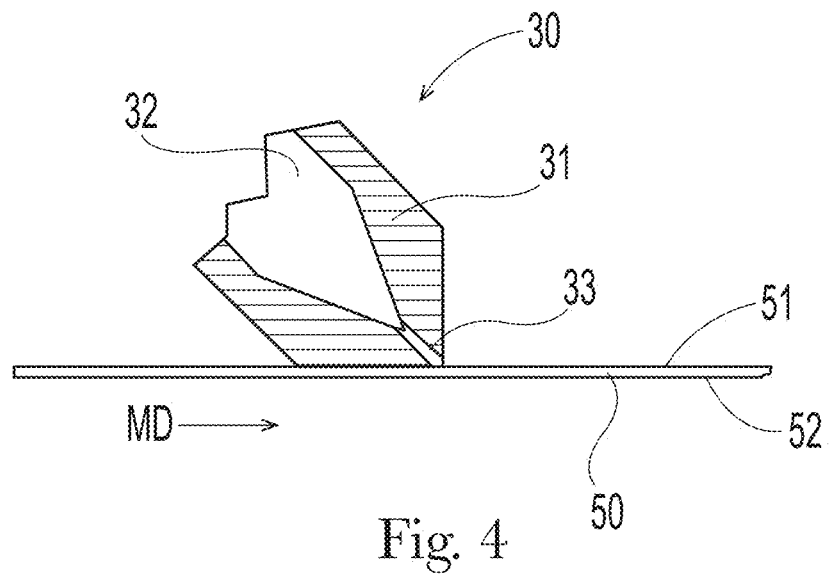
FIG. 4 is a schematic representation of an example of a method for treating a fibrous structure according to the present invention using a slot extrusion die.

In one example as shown in FIG. 4, a method for treating a fibrous structure comprises using a slot extrusion die 30, for example a jet extrusion die, which comprises a body 31, an internal fluid reservoir 32, and a pre-jet channel 33. A quaternary ammonium compound composition of the present invention may be applied from the internal fluid reservoir 32 through the pre-jet channel 33 to a fibrous structure 50 during converting of the fibrous structure 50. The quaternary ammonium compound composition may be applied to the first surface 51 and/or the second surface 52.

Figure 5:
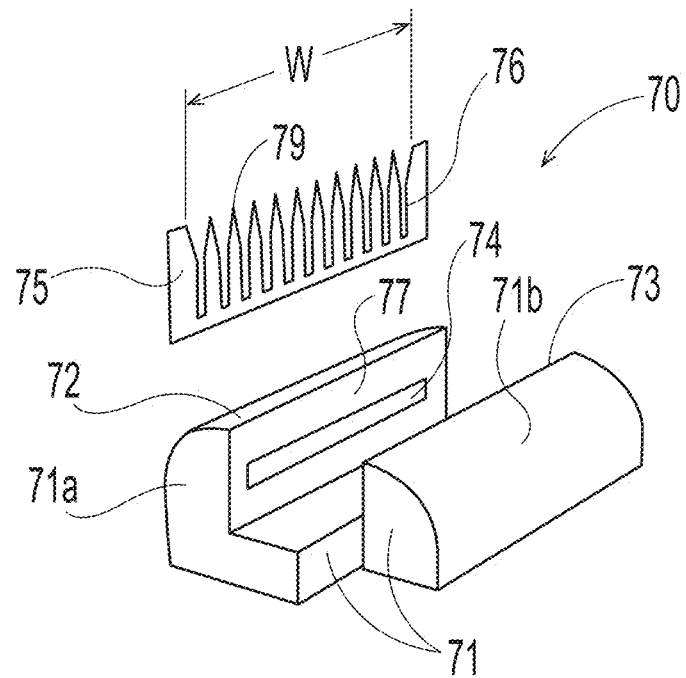
FIG. 5 is an exploded view of the slot extrusion die of FIG. 4.

As shown in FIG. 5, another example of an extrusion die 70 suitable for use in treating a fibrous structure according to the present invention comprises a body 71, for example a body 71 formed by a pair of portions 71a and 71b, at least one outlet lip 72, 73, a distribution channel 74, a shim 75 which is clamped between portions 71a and 71b, wherein the shim 75 comprises a plurality of slots 76, an inner face 77 of portion 71a, and an edge 79.

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means sheets, flats from roll stock, pre-converted flats, and/or single or multi-ply products unless otherwise stated. All tests are conducted in such conditioned room. Do not test samples that have defects such as wrinkles, tears, holes, and like. All instruments are calibrated according to manufacturer's specifications.

Basis Weight Test Method for Toilet Tissue Samples

Basis weight of a fibrous structure and/or sanitary tissue product is measured on stacks of twelve usable units using a top loading analytical balance with a resolution of ±0.001 g. The balance is protected from air drafts and other disturbances using a draft shield. A precision cutting die, measuring 3.500 in ±0.007 in by 3.500 in ±0.007 in is used to prepare all samples.

Stack six usable units aligning any perforations or folds on the same side of stack. With a precision cutting die, cut the stack into squares. Select six more usable units of the sample; stack and cut in like manner Combine the two stacks to form a single stack twelve squares thick. Measure the mass of the sample stack and record the result to the nearest 0.001 g.

The Basis Weight is calculated in lbs/3000 ft$^2$ or g/m$^2$ as follows:

Basis Weight=(Mass of stack)/[(Area of 1 layer in stack)×(Number of layers)]

For example,

Basis Weight (lbs/3000 ft$^2$)=[[Mass of stack (g)/453.6 (g/lbs)]/[12.25 (in$^2$)/144 (in$^2$/ft$^2$)×12]]×3000

Or,

Basis Weight (g/m$^2$)=Mass of stack (g)/[79.032 (cm$^2$)/10,000 (cm$^2$/m$^2$)×12]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

Basis Weight Test Method for Paper Towel Samples

Basis weight of a fibrous structure and/or sanitary tissue product is measured on stacks of twelve usable units using a top loading analytical balance with a resolution of ±0.001 g. The balance is protected from air drafts and other disturbances using a draft shield. A precision cutting die, measuring 4.000 in ±0.008 in by 4.000 in ±0.008 in is used to prepare all samples.

Stack eight usable units aligning any perforations or folds on the same side of stack. With a precision cutting die, cut the stack into squares. Measure the mass of the sample stack and record the result to the nearest 0.001 g.

The Basis Weight is calculated in lbs/3000 ft$^2$ or g/m$^2$ as follows:

Basis Weight=(Mass of stack)/[(Area of 1 layer in stack)×(Number of layers)]

For example,

Basis Weight (lbs/3000 ft$^2$)=[[Mass of stack (g)/453.6 (g/lbs)]/[16 (in$^2$)/144 (in$^2$/ft$^2$)×8]]×3000

Or,

Basis Weight (g/m$^2$)=Mass of stack (g)/[103.23 (cm$^2$)/10,000 (cm$^2$/m$^2$)×8]

Report result to the nearest 0.1 lbs/3000 ft$^2$ or 0.1 g/m$^2$. Sample dimensions can be changed or varied using a similar precision cutter as mentioned above, so as at least 100 square inches of sample area in stack.

Caliper Test Method

Caliper of a sanitary tissue product or web is measured using a ProGage Thickness Tester (Thwing-Albert Instrument Company, West Berlin, N.J.) with a pressure foot diameter of 2.00 inches (area of 3.14 in$^2$) at a pressure of 95 g/in$^2$. Four (4) samples are prepared by cutting of a usable unit such that each cut sample is at least 2.5 inches per side, avoiding creases, folds, and obvious defects. An individual specimen is placed on the anvil with the specimen centered underneath the pressure foot. The foot is lowered at 0.03 in/sec to an applied pressure of 95 g/in$^2$. The reading is taken after 3 sec dwell time, and the foot is raised. The measure is repeated in like fashion for the remaining 3 specimens. The caliper is calculated as the average caliper of the four specimens and is reported in mils (0.001 in) to the nearest 0.1 mils.

Dry Tensile Strength Test Method for Toilet Tissue Samples

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the load cell. Both the movable (upper) and stationary (lower) pneumatic jaws are fitted with smooth stainless steel faced grips, with a design suitable for testing 1 inch wide sheet material (Thwing-Albert item #733GC). An air pressure of about 60 psi is supplied to the jaws.

Twenty usable units of sanitary tissue product or web are divided into four stacks of five usable units each. The usable units in each stack are consistently oriented with respect to machine direction (MD) and cross direction (CD). Two of the stacks are designated for testing in the MD and two for CD. Using a one inch precision cutter (Thwing Albert) take a CD stack and cut two, 1.00 in ±0.01 in wide by at least 3.0 in long strips from each CD stack (long dimension in CD). Each strip is five usable unit layers thick and will be treated as a unitary specimen for testing. In like fashion cut the remaining CD stack and the two MD stacks (long dimension in MD) to give a total of 8 specimens (five layers each), four CD and four MD.

Program the tensile tester to perform an extension test, collecting force and extension data at an acquisition rate of 20 Hz as the crosshead raises at a rate of 4.00 in/min (10.16 cm/min) until the specimen breaks. The break sensitivity is set to 50%, i.e., the test is terminated when the measured force drops to 50% of the maximum peak force, after which the crosshead is returned to its original position.

Set the gage length to 2.00 inches. Zero the crosshead and load cell. Insert the specimen into the upper and lower open grips such that at least 0.5 inches of specimen length is contained each grip. Align specimen vertically within the upper and lower jaws, then close the upper grip. Verify specimen is aligned, then close lower grip. The specimen should be under enough tension to eliminate any slack, but less than 0.05 N of force measured on the load cell. Start the tensile tester and data collection. Repeat testing in like fashion for all four CD and four MD specimens.

Program the software to calculate the following from the constructed force (g) verses extension (in) curve:

Tensile Strength is the maximum peak force (g) divided by the product of the specimen width (1 in) and the number of usable units in the specimen (5), and then reported as g/M to the nearest 1 g/M.

Adjusted Gage Length is calculated as the extension measured at 11.12 g of force (in) added to the original gage length (in).

Elongation is calculated as the extension at maximum peak force (in) divided by the Adjusted Gage Length (in) multiplied by 100 and reported as % to the nearest 0.1%.

Tensile Energy Absorption (TEA) is calculated as the area under the force curve integrated from zero extension to the extension at the maximum peak force (g*in), divided by the product of the adjusted Gage Length (in), specimen width (in), and number of usable units in the specimen (5). This is reported as $g*in/in^2$ to the nearest 1 $g*in/in^2$.

Replot the force (g) verses extension (in) curve as a force (g) verses strain curve. Strain is herein defined as the extension (in) divided by the Adjusted Gage Length (in).

Program the software to calculate the following from the constructed force (g) verses strain curve:

Tangent Modulus is calculated as the least squares linear regression using the first data point from the force (g) verses strain curve recorded after 190.5 g (38.1 g×5 layers) force and the 5 data points immediately preceding and the 5 data points immediately following it. This slope is then divided by the product of the specimen width (2.54 cm) and the number of usable units in the specimen (5), and then reported to the nearest 1 g/cm.

The Tensile Strength (g/in), Elongation (%), TEA ($g*in/in^2$) and Tangent Modulus (g/cm) are calculated for the four CD specimens and the four MD specimens. Calculate an average for each parameter separately for the CD and MD specimens.

Calculations:

Geometric Mean Tensile=Square Root of [MD Tensile Strength (g/in)×CD Tensile Strength (g/in)]

Geometric Mean Peak Elongation=Square Root of [MD Elongation (%)×CD Elongation (%)]

Geometric Mean TEA=Square Root of [MD TEA ($g*in/in^2$)×CD TEA ($g*in/in^2$)]

Geometric Mean Modulus=Square Root of [MD Modulus (g/cm)×CD Modulus (g/cm)]

Total Dry Tensile Strength (TDT)=MD Tensile Strength (g/in)+CD Tensile Strength (g/in)

Total TEA=MD TEA ($g*in/in^2$)+CD TEA ($g*in/in^2$)

Total Modulus=MD Modulus (g/cm)+CD Modulus (g/cm)

Tensile Ratio=MD Tensile Strength (g/in)/CD Tensile Strength (g/in)

Dry Tensile Strength Test Method for Paper Towel Samples

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the load cell. Both the movable (upper) and stationary (lower) pneumatic jaws are fitted with smooth stainless steel faced grips, with a design suitable for testing 1 inch wide sheet material (Thwing-Albert item #733GC). An air pressure of about 60 psi is supplied to the jaws.

Eight usable units of sanitary tissue product or web are divided into two stacks of four usable units each. The usable units in each stack are consistently oriented with respect to machine direction (MD) and cross direction (CD). One of the stacks is designated for testing in the MD and the other for CD. Using a one inch precision cutter (Thwing Albert) take a CD stack and cut one, 1.00 in ±0.01 in wide by at least 5.0 in long stack of strips (long dimension in CD). In like fashion cut the remaining stack in the MD (strip long dimension in MD), to give a total of 8 specimens, four CD and four MD strips. Each strip to be tested is one usable unit thick and will be treated as a unitary specimen for testing.

Program the tensile tester to perform an extension test, collecting force and extension data at an acquisition rate of 20 Hz as the crosshead raises at a rate of 4.00 in/min (10.16 cm/min) until the specimen breaks. The break sensitivity is set to 50%, i.e., the test is terminated when the measured force drops to 50% of the maximum peak force, after which the crosshead is returned to its original position.

Set the gage length to 4.00 inches. Zero the crosshead and load cell. Insert the specimen into the upper and lower open grips such that at least 0.5 inches of specimen length is contained each grip. Align specimen vertically within the upper and lower jaws, then close the upper grip. Verify specimen is aligned, then close lower grip. The specimen should be under enough tension to eliminate any slack, but less than 0.05 N of force measured on the load cell. Start the tensile tester and data collection. Repeat testing in like fashion for all four CD and four MD specimens.

Program the software to calculate the following from the constructed force (g) verses extension (in) curve:

Tensile Strength is the maximum peak force (g) divided by the specimen width (1 in), and reported as g/M to the nearest 1 g/M.

Adjusted Gage Length is calculated as the extension measured at 11.12 g of force (in) added to the original gage length (in).

Elongation is calculated as the extension at maximum peak force (in) divided by the Adjusted Gage Length (in) multiplied by 100 and reported as % to the nearest 0.1%.

Tensile Energy Absorption (TEA) is calculated as the area under the force curve integrated from zero extension to the extension at the maximum peak force (g*in), divided by the product of the adjusted Gage Length (in) and specimen width (in). This is reported as $g*in/in^2$ to the nearest 1 $g*in/in^2$.

Replot the force (g) verses extension (in) curve as a force (g) verses strain curve. Strain is herein defined as the extension (in) divided by the Adjusted Gage Length (in).

Program the software to calculate the following from the constructed force (g) verses strain curve:

Tangent Modulus is calculated as the least squares linear regression using the first data point from the force (g) verses strain curve recorded after 38.1 g force and the 5 data points immediately preceding and the 5 data points immediately following it. This slope is then divided by the specimen width (2.54 cm), and then reported to the nearest 1 g/cm.

The Tensile Strength (g/in), Elongation (%), TEA ($g*in/in^2$) and Tangent Modulus (g/cm) are calculated for the four CD specimens and the four MD specimens. Calculate an average for each parameter separately for the CD and MD specimens.

Calculations:

Geometric Mean Tensile=Square Root of [MD Tensile Strength (g/in)×CD Tensile Strength (g/in)]

Geometric Mean Peak Elongation=Square Root of [MD Elongation (%)×CD Elongation (%)]

Geometric Mean TEA=Square Root of [MD TEA ($g*in/in^2$)×CD TEA ($g*in/in^2$)]

Geometric Mean Modulus=Square Root of [MD Modulus (g/cm)×CD Modulus (g/cm)]

Total Dry Tensile Strength (TDT)=MD Tensile
Strength (g/in)+CD Tensile Strength (g/in)

Total TEA=MD TEA (g*in/in$^2$)+CD TEA (g*in/in$^2$)

Total Modulus=MD Modulus (g/cm)+CD Modulus
(g/cm)

Tensile Ratio=MD Tensile Strength (g/in)/CD Tensile Strength (g/in)

Wet Tensile Test Method

The Wet Tensile Strength test method is utilized for the determination of the wet tensile strength of a sanitary tissue product or web strip after soaking with water, using a tensile-strength-testing apparatus operating with a constant rate of elongation. The Wet Tensile Strength test is run according to ISO 12625-5:2005, except for any deviations or modifications described below. This method uses a vertical tensile-strength tester, in which a device that is held in the lower grip of the tensile-strength tester, called a Finch Cup, is used to achieve the wetting.

Using a one inch JDC precision sample cutter (Thwing Albert) cut six 1.00 in ±0.01 in wide strips from a sanitary tissue product sheet or web sheet in the machine direction (MD), and six strips in the cross machine direction (CD). An electronic tensile tester (Model 1122, Instron Corp., or equivalent) is used and operated at a crosshead speed of 1.0 inch (about 1.3 cm) per minute and a gauge length of 1.0 inch (about 2.5 cm). The two ends of the strip are placed in the upper jaws of the machine, and the center of the strip is placed around a stainless steel peg. The strip is soaked in distilled water at about 20° C. for the identified soak time, and then measured for peak tensile strength. Reference to a machine direction means that the sample being tested is prepared such that the length of the strip is cut parallel to the machine direction of manufacture of the product.

The MD and CD wet peak tensile strengths are determined using the above equipment and calculations in the conventional manner. The reported value is the arithmetic average of the six strips tested for each directional strength to the nearest 0.1 grams force. The total wet tensile strength for a given soak time is the arithmetic total of the MD and CD tensile strengths for that soak time. Initial total wet tensile strength ("ITWT") is measured when the paper has been submerged for 5±0.5 seconds. Decayed total wet tensile ("DTWT") is measured after the paper has been submerged for 30±0.5 minutes.

Wet Decay Test Method

Wet decay (loss of wet tensile) for a sanitary tissue product or web is measured according to the Wet Tensile Test Method described herein and is the wet tensile of the sanitary tissue product or web after it has been standing in the soaked condition in the Finch Cup for 30 minutes. Wet decay is reported in units of "%". Wet decay is the % loss of Initial Total Wet Tensile after the 30 minute soaking.

Dry Burst Test Method

The Dry Burst Test is run according to ISO 12625-9:2005, except for any deviations described below. Sanitary tissue product samples or web samples for each condition to be tested are cut to a size appropriate for testing, a minimum of five (5) samples for each condition to be tested are prepared.

A burst tester (Burst Tester Intelect-II-STD Tensile Test Instrument, Cat. No. 1451-24PGB available from Thwing—Albert Instrument Co., Philadelphia, Pa., or equivalent) is set up according to the manufacturer's instructions and the following conditions: Speed: 12.7 centimeters per minute; Break Sensitivity: 20 grams; and Peak Load: 2000 grams. The load cell is calibrated according to the expected burst strength.

A sanitary tissue product sample or web sample to be tested is clamped and held between the annular clamps of the burst tester and is subjected to increasing force that is applied by a 0.625 inch diameter, polished stainless steel ball upon operation of the burst tester according to the manufacturer's instructions. The burst strength is that force that causes the sample to fail.

The burst strength for each sanitary tissue product sample or web sample is recorded. An average and a standard deviation for the burst strength for each condition is calculated.

The Dry Burst is reported as the average and standard deviation for each condition to the nearest gram.

Wet Burst Test Method

"Wet Burst Strength" as used herein is a measure of the ability of a sanitary tissue product or web to absorb energy, when wet and subjected to deformation normal to the plane of the sanitary tissue product or web. The Wet Burst Test is run according to ISO 12625-9:2005, except for any deviations or modifications described below.

Wet burst strength may be measured using a Thwing-Albert Burst Tester Cat. No. 177 equipped with a 2000 g load cell commercially available from Thwing-Albert Instrument Company, Philadelphia, Pa., or an equivalent instrument.

Wet burst strength is measured by preparing four (4) sanitary tissue product samples or web samples for testing. First, condition the samples for two (2) hours at a temperature of 73° F.±2° F. (23° C.±1° C.) and a relative humidity of 50% (±2%). Take one sample and horizontally dip the center of the sample into a pan filled with about 25 mm of room temperature distilled water. Leave the sample in the water four (4) (±0.5) seconds. Remove and drain for three (3) (±0.5) seconds holding the sample vertically so the water runs off in the cross machine direction. Proceed with the test immediately after the drain step.

Place the wet sample on the lower ring of the sample holding device of the Burst Tester with the outer surface of the sample facing up so that the wet part of the sample completely covers the open surface of the sample holding ring. If wrinkles are present, discard the samples and repeat with a new sample. After the sample is properly in place on the lower sample holding ring, turn the switch that lowers the upper ring on the Burst Tester. The sample to be tested is now securely gripped in the sample holding unit. Start the burst test immediately at this point by pressing the start button on the Burst Tester. A plunger will begin to rise (or lower) toward the wet surface of the sample. At the point when the sample tears or ruptures, report the maximum reading. The plunger will automatically reverse and return to its original starting position. Repeat this procedure on three (3) more samples for a total of four (4) tests, i.e., four (4) replicates. Report the results as an average of the four (4) replicates, to the nearest gram.

Viscosity Test Method

Objective:

Obtain a fluid viscosity measurement of a formulation or other fluid material.

Equipment:

Brookfield DVEE LV TJ

Spindle No. SC 421

Sample container—SC 4

Spindle Speed—100 rpm

Temperature of Sample—23° C.±2° C.

General Information:
  Viscosity appears in units of Poise (shown as "P"), centipoise (shown as "cP"), Pascal Seconds (shown as "Pa·S") or milliPascal-seconds (shown as "mPa·s") on the DVE display.
  Torque appears in units of dyne-centimeters or Newton-meters (shown as percent "%" in both cases) on the DVE display.
The equivalent units of measurement in the SI system are calculated using the following conversions:

|  | SI | CGS |
|---|---|---|
| Viscosity: | 1 mPa · s= | 1 cP |
| Torque: | 1 Newton-m= | 107 dyne-cm |
|  |  | 1 Pa · S = 10 P |

Procedure:
1. Check to insure viscometer is level (examine bubble on front of instrument). Adjust as necessary using the three leveling screws on the bottom of the base.
2. Turn on the instrument.
3. Select spindle to be used. The process of selecting a spindle and speed for an unknown fluid is normally trial and error. An appropriate selection will result in measurements between 10-100 on the instrument % torque scale.
4. Place fluid to be measured in a container. It is recommended you use the appropriate container for the selected spindle). Alternate containers may be used, but may affect results. Note container used when reporting results.
5. Attach Spindle:
   a. Be sure the motor is off when changing spindles.
   b. Attach guard leg if desired.
   c. Attach the spindle to the lower shaft. Lift the shaft slightly, holding it firmly with one hand while screwing the spindle on with the other (NOTE: Left-handed threads). Avoid putting side thrust on the shaft.
   d. With a disc-type spindle, it is necessary to tilt the spindle slightly while immersing to avoid trapping air bubbles under the surface of the disc. You may find it more convenient to immerse the spindle in this fashion before attaching it to the viscometer.
   e. Center the spindle in the test material.
   f. The spindle should be inserted to the immersion groove located on the spindle shaft. Use the laboratory stand clamp to adjust the height of the viscometer.
6. Enter the spindle number into the DVE Viscometer by using the SPINDLE UP/DOWN key.
7. Select the speed of rotation by using the SPEED UP/DOWN key. At speeds of 1 RPM and lower, additional time may be required to allow for complete deflection of the torque sensor. The % (torque) and cP (viscosity) will flash until 2 revolutions are achieved and the % torque value is greater than 10%.
8. To make a viscosity measurement, press the MOTOR ON/OFF key. Allow time for the indicated reading to stabilize.
   a. The DVE gives indications for out of specification or out of range operation. When torque % readings exceed 100.0% (over range), the display changes to EEEE cP & EEEE %. You must either reduce the speed or use a smaller size spindle to correct this condition.
   b. If you operate at spindle speeds that produce torque below 10.0% (under-range), the DVE displays both torque % and viscosity (cP) with flashing unit designations. You must either increase speed or use a larger size spindle to correct this condition. For maximum accuracy, flashing readings below 10% should be avoided.
9. The test is stopped by pressing the MOTOR ON/OFF key. The display will hold the last measured torque value and measured viscosity.
10. If desired that data be collected at more than one speed, change the speed of rotation during the test.
11. Record the % Torque and viscosity. Also record and report the spindle type, speed, temperature, container description, and test length.
12. Remove the spindle and guard leg (if used) before cleaning. Remember to secure the viscometer shaft and lift up slightly while removing the spindle.
13. Clean the spindles and guard leg after each use. Spindles and guard leg are made of stainless steel. Typical cleaning procedure: Rinse off spindle and guard leg with tap water. Shake off water and dry with a non-abrasive cloth. Wipe a second time using a solvent appropriate for sample material that is not aggressive to stainless steel (e.g. alcohol wipe 70/30).
14. Turn off instrument when testing is complete.

Average Particle Size Distribution Test Method
Objective:
  Obtain images and average particle size distribution on sample compositions.
Equipment:
ZEISS AXIO Scope.A1
Microscope slides & cover slips
ZEN 2 Core software
Procedure:
1. Turn on microscope.
2. Turn on computer and launch software.
3. Obtain sample for analysis.
4. Deposit small amount of sample onto a microscope slide and carefully add cover slip to avoid trapping too much air.
5. Place slide on stage.
6. Remove eyepiece and diaphragm covers.
7. Rotate nosepiece to select desired objective.
8. Turn condenser ring to BF.
9. Adjust light intensity control, diaphragm, condenser, and focusing drives to obtain best image.
10. Use gear knobs to move stage and choose view to image.
11. Flip switch to move to camera use.
12. Click button to view live image.
13. Under microscope configuration select correct objective.
14. Focus image as necessary using microscope. Adjust camera settings (e.g. white balance) using software.
15. Click snap to take image. Using software, make measurements of particles to calculate average particle size distribution and save images.
16. If necessary, the sample images can be obtained under cross polar conditions by moving polarizer into place and adjusting to obtain images.
17. Analyze and measure the particles as described in Step 15 above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A quaternary ammonium compound composition comprising:
   a. greater than 25% by weight of a quaternary ammonium compound; and
   b. less than 75% by weight of water;
   wherein the quaternary ammonium compound composition exhibits an average particle size distribution of from about 100 nm to about 50 µm as measured according to the Average Particle Size Distribution Test Method such that the quaternary ammonium compound composition exhibits a viscosity of less than 250 cP after 14 days as measured according to the Viscosity Test Method..

2. The quaternary ammonium compound composition according to claim 1 wherein the quaternary ammonium compound is selected from the group consisting of: quaternary ammonium compounds that exhibit a melting point of greater than 30° C.

3. The quaternary ammonium compound composition according to claim 1 wherein the quaternary ammonium compound has the formula:

Formula I

wherein:
m is 1 to 3; each $R^1$ is independently a $C_1$-$C_6$ alkyl group, hydroxyalkyl group, hydrocarbyl or substituted hydrocarbyl group, alkoxylated group, benzyl group, alkenyl group, or mixtures thereof; each $R^2$ is independently a $C_{14}$-$C_{22}$ alkyl group, hydroxyalkyl group, hydrocarbyl or substituted hydrocarbyl group, alkoxylated group, benzyl group, alkenyl group, or mixtures thereof; and $X^-$ is a compatible anion.

4. The quaternary ammonium compound composition according to claim 3 wherein each $R^1$ is independently a $C_1$-$C_6$ alkyl or alkenyl group or mixtures thereof.

5. The quaternary ammonium compound composition according to claim 3 wherein each $R^2$ is independently a $C_{16}$-$C_{18}$ alkyl or alkenyl group or mixtures thereof.

6. The quaternary ammonium compound composition according to claim 1 wherein the quaternary ammonium compound has the formula:

wherein:
Y is independently —O—(O)C—, —C(O)—O—, —NH—C(O)—, or —C(O)—NH—, or mixtures thereof; m is 1 to 3; n is 0 to 4; each $R^1$ is independently a $C_1$-$C_6$ alkyl group, hydroxyalkyl group, hydrocarbyl or substituted hydrocarbyl group, alkoxylated group, benzyl group, alkenyl group, or mixtures thereof; each $R^3$ is independently a $C_{13}$-$C_{21}$ alkyl group, hydroxyalkyl group, hydrocarbyl or substituted hydrocarbyl group, alkoxylated group, benzyl group, alkenyl group, or mixtures thereof, and $X^-$ is a compatible anion.

7. The quaternary ammonium compound composition according to claim 6 wherein the quaternary ammonium compound is selected from the group consisting of: dialkyldialkylammonium salts and mixtures thereof.

8. The quaternary ammonium compound composition according to claim 6 wherein the quaternary ammonium compound is selected from the group consisting of: diester ditallow dimethyl ammonium chloride, diester distearyl dimethyl ammonium chloride, monoester ditallow dimethyl ammonium chloride, diester di(hydrogenated)tallow dimethyl ammonium methyl sulfate, diester di(hydrogenated)tallow dimethyl ammonium chloride, monoester di(hydrogenated)tallow dimethyl ammonium chloride, diester di(non hydrogenated)tallow dimethyl ammonium chloride, diester di(touch hydrogenated)tallow dimethyl ammonium chloride, diester di(hydrogenated)tallow dimethyl ammonium chloride, and mixtures thereof.

9. The quaternary ammonium compound composition according to claim 1 wherein the quaternary ammonium compound composition comprises greater than 30% by weight of the quaternary ammonium compound.

10. The quaternary ammonium compound composition according to claim 1 wherein the quaternary ammonium compound composition comprises less than 70% by weight of water.

11. The quaternary ammonium compound composition according to claim 1 wherein the quaternary ammonium compound composition exhibits an average particle size distribution of from about 100 µm to about 50 µm as measured according to the Average Particle Size Distribution Test Method.

12. The quaternary ammonium compound composition according to claim 1 wherein the quaternary ammonium compound composition further comprises one or more surfactants.

13. The quaternary ammonium compound composition according to claim 1 wherein the quaternary ammonium compound composition comprises a plurality of vesicles dispersed throughout a continuous phase comprising the water.

14. The quaternary ammonium compound composition according to claim 13 wherein the vesicles comprise the quaternary ammonium compound.

15. A quaternary ammonium compound composition comprising:
  a. greater than 25% but less than 40% by weight of a quaternary ammonium compound; and
  b. greater than 60% to less than 75% by weight of water;
  wherein the quaternary ammonium compound composition exhibits aan average particle size distribution of from about 100 nm to about 50 μm as measured according to the Average Particle Size Distribution Test Method.

16. A quaternary ammonium compound composition comprising:
  a. greater than 25% but less than 40% by weight of a quaternary ammonium compound;
  b. less than 75% by weight of water; and
  c. salt;
  wherein the quaternary ammonium compound composition exhibits an average particle size distribution of from about 100 nm to about 50 μm as measured according to the Average Particle Size Distribution Test Method.
  c. adding water, for example water comprising a salt to dilute the level of the quaternary ammonium compound in the quaternary ammonium compound composition to less than 40%.

17. A fibrous structure comprising a surface comprising a dewatered form of the quaternary ammonium compound composition according to claim 1.

* * * * *